US011857650B2

(12) United States Patent
Weber et al.

(10) Patent No.: US 11,857,650 B2
(45) Date of Patent: Jan. 2, 2024

(54) DENTAL COMPOSITION COMPRISING A DENTAL FILLER CONTAINING A STRUCTURAL FILLER AND SILANATED GLASS FLAKES

(71) Applicant: DENTSPLY SIRONA inc., York, PA (US)

(72) Inventors: Christoph Weber, Constance (DE); Uwe Walz, Constance (DE); Stephanie Noerpel, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 1379 days.

(21) Appl. No.: 16/313,935

(22) PCT Filed: Jun. 30, 2017

(86) PCT No.: PCT/EP2017/066323
§ 371 (c)(1),
(2) Date: Dec. 28, 2018

(87) PCT Pub. No.: WO2018/002326
PCT Pub. Date: Jan. 4, 2018

(65) Prior Publication Data
US 2019/0231648 A1    Aug. 1, 2019

(30) Foreign Application Priority Data

Jun. 30, 2016    (EP) ..................................... 16177317

(51) Int. Cl.
*A61K 6/77*    (2020.01)
*A61K 6/17*    (2020.01)
(Continued)

(52) U.S. Cl.
CPC .................. *A61K 6/77* (2020.01); *A61K 6/17* (2020.01); *A61K 6/61* (2020.01); *A61K 6/62* (2020.01);
(Continued)

(58) Field of Classification Search
CPC . A61K 6/77; A61K 6/887; A61K 6/61; A61K 6/17
See application file for complete search history.

(56) References Cited

U.S. PATENT DOCUMENTS 3,655,605 A    4/1972  Smith
3,814,717 A    6/1974  Wilson
(Continued)

FOREIGN PATENT DOCUMENTS

CN    101405333 A    4/2009
EP    0173567 A2     3/1986
(Continued)

OTHER PUBLICATIONS

Mohseni et al, "Effect of plate-like glass fillers on the mechanical properties of dental nanocomposites", Iranian Polymer Journal, vol. 25, Issue 2, Dec. 15, 2015, pp. 129-134.*
(Continued)

*Primary Examiner* — C Melissa Koslow
(74) *Attorney, Agent, or Firm* — DENTSPLY SIRONA INC.

(57) ABSTRACT

The present invention relates to a dental composition comprising a dental filler containing a structural filler and silanated glass flakes. Furthermore, the present invention relates to the use of silanated glass flakes for preparing a dental composition.

14 Claims, 5 Drawing Sheets

(51) Int. Cl.
| | |
|---|---|
| *A61K 6/61* | (2020.01) |
| *A61K 6/62* | (2020.01) |
| *A61K 6/802* | (2020.01) |
| *A61K 6/816* | (2020.01) |
| *A61K 6/887* | (2020.01) |
| *C03C 3/087* | (2006.01) |
| *C03C 3/093* | (2006.01) |
| *C08L 33/10* | (2006.01) |

(52) U.S. Cl.
CPC .............. *A61K 6/802* (2020.01); *A61K 6/816* (2020.01); *A61K 6/887* (2020.01); *C03C 3/087* (2013.01); *C03C 3/093* (2013.01); *C08L 33/10* (2013.01)

(56) References Cited

U.S. PATENT DOCUMENTS

| | | | |
|---|---|---|---|
| 4,143,018 | A | 3/1979 | Crisp |
| 4,209,434 | A | 6/1980 | Crisp |
| 4,298,738 | A | 11/1981 | Lechtken |
| 4,324,744 | A | 4/1982 | Lechtken |
| 4,360,605 | A | 11/1982 | Schmitt |
| 4,376,835 | A | 3/1983 | Schmitt |
| 4,385,109 | A | 5/1983 | Lechtken |
| 4,814,362 | A | 3/1989 | Billington |
| 5,154,762 | A | 10/1992 | Mitra |
| 5,318,929 | A | 6/1994 | Jana |
| 5,360,770 | A | 11/1994 | Chadwick |
| 5,501,727 | A | 3/1996 | Wang |
| 5,545,676 | A | 8/1996 | Palazzotto |
| 2004/0079258 | A1 | 4/2004 | Hoescheler |
| 2006/0241205 | A1 | 10/2006 | Jia |
| 2009/0088515 | A1 | 4/2009 | Yagyu |

FOREIGN PATENT DOCUMENTS

| | | | |
|---|---|---|---|
| EP | 1548021 | A1 | 6/2005 |
| EP | 2604247 | A1 | 6/2013 |
| EP | 2705827 | A1 | 3/2014 |
| EP | 2727576 | A1 | 5/2014 |
| GB | 2441441 | A | 3/2008 |
| WO | 9917716 | A2 | 4/1999 |
| WO | 0150974 | A1 | 7/2001 |
| WO | 0150976 | A2 | 7/2001 |
| WO | 2017006302 | A1 | 1/2017 |

OTHER PUBLICATIONS

Datasheet of ECR Glassflage, grade GF350nmM, supplied by Glass Flake Ltd, Leeds, UK.
"Reinforcement of poly(methyl methacrylate) denture base with glass flake"; Franklin P. et al; Dental Materials, Elsevier, Amsterdam, NL; vol. 21, No. 4; Apr. 1, 2005; pp. 365-370.
"Flexural properties and impact strength of denture base resins reinforced with micronized glass flakes"; Choksi Ronak H. et al; The Journal of Indian Prosthodontic Society; vol. 16, No. 3; Jul. 18, 2016; pp. 264-270.
"Craig's Restorative Dental Materials"; Sakaguchi Ronald et al; 13th Edition, Elsevier Mosby; 2012.
European Office Action dated Mar. 18, 2022.
"The tooth-coloured restorative Materials III: Glass ionomer cements" S.J. Bonsor; "A Clinical Guide to applied Dental Materials"; Elsevier Health Sciences, 2012, 1st Edition, p. 105.
"The Influence of Polymerization Type and Reinforcement Method on Flexural Strength of Acrylic Resin" R.B. Fonseca et al., The Scientific World Journal, vol. 2015, Hindawi Publishing Corporation, pp. 1 to 8.
Written Opinion of the International Searching Authority; PCT/EP2017/066323; Oct. 13, 2017 (completed); dated Oct. 20, 2017 (mailed).
"The effect of glass flakes reinforcement on the surface hardness and surface roughness of heat-cured poly (methyl methacrylate) denture base material"; Abdulrazzaq et al.; J. Bagh College Dentistry, vol. 27 (2), Jun. 2015, pp. 6 to 10.
"Application of flake shaped glass (Glass Flake®) filler for dental composite resin"; M. Uo Et al., Journal of the Ceramic Society of Japan, vol. 118, No. 6, 2010, pp. 425 to 427.
"Effect of plate-like glass fillers on the mechanical properties of dental nanocomposites"; M. Mohseni et al., Iranian Polymer Journal, vol. 25, issue 2 pp. 129 to 134, Dec. 15, 2015.
"Resistance to impact of cross-linked denture base biopolymer materials: Effect of relining, glass flakes reinforcement and cyclic loading"; L.E. da Cruz Perez et al.; Journal of the Mechanical Behavior of Biomedical Materials, vol. 37 (2014), pp. 33 to 41.
"Glass Ionomer Cement Formulations: I. The Preparation of Novel Fluoroaluminosilicate Glasses High in Fluorine"; Journal of Dental Research; Jun. 1979; pp. 1607-1619.
"Chemistry of Silanes: Interfaces in Dental Polymers and Composites"; J.M. Antonucci; Journal of Research of the National Institute of Standards and Technology, 2005; vol. 110, No. 5; pp. 541 to 558.
"Preparation of Substituted Benzoyltrimethylsilanes by the Palladium-Catalyzed Silylation of Substituted Benzoyl Chlorides with Hexamethyldisilane"; K. Yamamoto et al., J. Tetrahedron Letters, 1980, vol. 21, pp. 1653 to 1656.
"Tert-Butyl Tert-Butyldimethysilylglyoxylate: A Useful Conjunctive Reagent"; Nicewicz D.A. et al; Organic Syntheses; 2008, 85 pp. 278 to 286.
"Three-Component Coupling Reactions of Silylglyoxylates, Alkynes, and Aldehydes: A Chemoselective One-Step Glycolate Aldol Construction"; Nicewicz D.A. in J. Am. Chem. Soc., 2005, 127 (17) pp. 6170 to 6171.
"Silyl Glyoxylates. Conception and Realization of Flexible Conjunctive Reagents for multicomponent Coupling"; Boyce G.R. et al.; The Journal of Organic Chemistry, 2012; vol. 77, No. 10; pp. 4503 to 4515.
"Construction of Cyclopentanol Derivatives via Three-Component Coupling of Silyl Glyoxylates, Acetylides, and Nitroalkenes" Boyce G.R. et al; Organic Letters, 2012; vol. 14, No. 2; pp. 652 to 655.
"A search for new radical sources in photoinitiating systems" El-Roz, M. et al. in Current Trends in Polymer Science, 2011, vol. 15, pp. 1 to 13.
Chinese Office Action dated Jun. 17, 2021.
European Office Action dated May 31, 2021.
International Search Report; PCT/EP2017/066323; Oct. 13, 2017 (completed); dated Oct. 20, 2017 (mailed).
International Preliminary Report on Patentability; PCT/EP2017/066323; Oct. 13, 2017 (completed); dated Oct. 20, 2017 (mailed).

\* cited by examiner

DENTAL COMPOSITION COMPRISING A DENTAL FILLER CONTAINING A STRUCTURAL FILLER AND SILANATED GLASS FLAKES

FIELD OF THE INVENTION

The present invention relates to a dental composition comprising a dental filler containing a structural filler and silanated glass flakes. Furthermore, the present invention relates to the use of silanated glass flakes for preparing a dental composition.

The dental composition according to the present invention provides a cured dental composition having excellent esthetic appearance, in particular in terms of gloss, wherein gloss retention is ensured for a long period of time, as well as excellent mechanical properties and long-term mechanical and chemical resistance. Furthermore, the uncured dental composition according to the invention has advantageous handling properties which may be based on thixotropic behaviour.

BACKGROUND OF THE INVENTION

Dental restorative materials are known for restoring the function, morphology and integrity of dental structures damaged by physical damage or caries-related decay of enamel and/or dentin. Dental restorative materials are required to have high biocompatibility, good mechanical properties and mechanical and chemical resistance over a long period of time given the harsh conditions for a restorative material in the oral cavity.

Dental restorative materials include dental compositions comprising a glass filler in the form of unreactive and/or reactive particulate glass fillers. Such glass fillers have good biocompatibility. Unreactive particulate glass fillers may be added for example for adjusting mechanical properties and optical appearance. Reactive particulate glass fillers may provide cariostatic properties through the release of fluoride ions, and they provide for a good adhesion to the dental hard tissues. Dental compositions comprising reactive particulate glass fillers are curable by an acid-base reaction between a reactive glass powder and a polyalkenoic acid.

Particulate glass fillers for use in dental compositions are often provided as particles having a small aspect ratio, for example, as spherical particles. Particles having a small aspect ratio may be obtained by wet or dry milling of a glass frit, and are commonly used in glass ionomer cement compositions, as disclosed e.g. in S. J. Bonsor, "A Clinical Guide to applied Dental Materials", Elsevier Health Sciences, 2012, 1$^{st}$ edition, page 105.

A particulate glass filler may also contain particles having a large aspect ratio, for example, fibers. Glass fibers may be used for improving mechanical properties such as flexural strength of the cured dental composition. Accordingly, glass fibers having a length of about 3 mm are used, as disclosed for example in R. B. Fonseca et al., The Scientific World Journal, Volume 2015, Hindawi Publishing Corporation, pages 1 to 8, and L. S. Acosta-Torres, published online by the Elsevier Editorial System™ for Dental Materials as manuscript draft.

Particulate glass fillers may also contain particles having a flake shape. H. T. Abdulrazzaq et al., J. Bagh College Dentistry, vol. 27(2), Jun. 2015, pages 6 to 10 discloses dental compositions containing a heat-curing denture base material and glass flakes pre-treated with a silane coupling agent, which glass flakes have a thickness of 1.3 to 2.3 µm, and a range of diameters of which 88% are below 50 µm. The heat-curing denture base material comprises methylmethacrylate, ethylenglycoldimethacrylate, poly(methylmethacrylate) and dibenzoylperoxide. The glass flakes were applied for reinforcing the surface hardness and surface roughness of a resulting heat-cured poly(methyl methacrylate) matrix.

M. Uo et al., Journal of the Ceramic Society of Japan, vol. 118, no. 6, 2010, pages 425 to 427 discloses a dental composition containing resin matrix in the form a mixture of A-diglycidyl methacrylate (Bis-GMA) and triethylene dimethacrylate (MMA), and glass flakes silanized with 3-methacryloxypropyl trimethoxysilane. The glass flakes have a thickness of 5 µm and a diameter of approximately 45 µm and were added for adjusting mechanical strength in terms of compressive strength and Vickers hardness and and estheticity in terms of optical transparency of the cured composition, and for adjusting relative flowability of the uncured composition.

US 2006/0241205 A1 discloses a dental restoration comprising a polymeric matrix precursor composition and glass flakes having a thickness in the range of about 1 to 10 µm and a length/width in the range of about 5 to 1000 µm. The dental restoration may comprise at least one additional filler material being at least one of silica, silicate glass, quartz, barium silicate, strontium silicate, barium borosilicate, borosilicate, lithium silicate, amorphous silica, ammoniated or deammoniated calcium phosphate, alumina, zirconia, tin oxide or titania. No general value range is disclosed for the additional filler. However, in the experimental examples, an additional filler in the form of a silane treated glass filler having 0.7 µm average particle size is disclosed. The glass flakes were added as reinforcing agent to obtain a cured dental composite material having good physical properties in terms of flexural strength, flexural modulus and Vickers hardness. Furthermore, it is disclosed that there would be a synergistic effect providing for particular improved flexural strength and flexural modulus in case the glass flakes are combined with glass fillers having a smaller particle size than the glass flakes.

GB 2 441 441 A suggests a dental composition containing a hardenable material and glass flakes having a thickness of up to 1000 nm, preferably 200 to 1000 nm, and an aspect ratio of at least 20:1. GB 2 441 441 A does not disclose silanized glass flakes or any details on further components of the dental composition. Glass flakes are suggested to provide resistance to shrinkage.

WO 01/50974 A1 discloses a polymerizable dental filling and sealing composition containing an inert filler material for adjusting the viscosity of the composition to an appropriate level for the introduction by syringing into a cavity having a diameter of less than 1 mm, and for increasing the biaxial strength of the resin. The inert filler material may be in the form of glass flakes which may be coated with a silane coupling agent, and which have a thickness of 0.5 to 10 µm and an aspect ratio of 5:1 and 10:1.

M. Mohseni et al., Iranian Polymer Journal, vol. 25, issue 2, pages 129 to 134 discloses a dental composition containing a matrix resin, silanized spherical nanosilica particles having a primary particle size of 40 nm, and silanized glass flakes ("GF100 nm" available from Glassflake Ltd. (UK)) having a thickness of about 100 nm. Glass flakes "GF100 nm" appear to have a particle size distribution wherein at least 80% of the particles have a particle size of 1700-150 µm. The effect of glass flakes on flexural modulus, flexural strength and fracture toughness of a cured dental composition is reported.

L. E. da Cruz Perez et al., Journal of the mechanical behaviour of biomedical materials, vol. 37 (2014), pages 33 to 41 discloses dental resin compositions containing acryl silane micronized glass flakes having a thickness of 1.9 to 2.5 μm. The effect of the glass flakes on relining, reinforcement and cyclic loading of a cured dental composition is reported.

WO 2017/006302 A1, which was published after the priority date of the present application, discloses a dental composition comprising glass flakes and a resin, wherein the glass flakes and resin have a refractive index difference of less than 0.04. The glass flakes preferably have a thickness in the range of between 0.5 and 10 microns and an aspect ratio in the range of between 14:1 and 90:1. For the cured dental composition, the effect of improved wear-resistance and aesthetic properties is reported.

SUMMARY OF THE INVENTION

It is an object of the present invention to provide a dental composition providing excellent gloss and gloss retention when cured, as well as having excellent mechanical properties including flexural strength and E-modulus, and long-term mechanical and chemical resistance. Furthermore, the uncured dental composition may have excellent handling properties based on thixotropic behaviour. Moreover, the uncured dental composition may also have excellent handling properties in terms of an advantageous extrusion force for extruding the uncured dental composition through a nozzle.

According to a first aspect, the present invention provides a dental composition comprising:
(i) a dental filler containing
  (A) a structural filler having an average particle size of from 0.1 to 3 μm; and
  (B) silanated glass flakes,
    (a) wherein the silanated glass flakes have an average thickness between 50 nm and 1000 nm; and
    (b) wherein the silanated glass flakes have an average aspect ratio (long diameter/thickness) in the range of from 2:1 to 50:1;
(ii) one or more polymerizable compounds; and
(iii) an initiator system.

According to a second aspect, the present invention provides a use of silanated glass flakes,
  (a) the silanated glass flakes having an average thickness between 50 nm and 1000 nm; and
  (b) the silanated glass flakes having an average aspect ratio in the range of from 2:1 to 50:1;
for preparing a dental composition, preferably a dental composition according to the first aspect.

The present invention is based on the recognition that excellent gloss and gloss retention properties of a cured dental composition may be provided by the use of a specific combination of a structural filler and silanated glass flakes. Moreover, the present invention is based on the recognition that excellent mechanical properties and long-term mechanical and chemical resistance may also be provided by the specific combination of a structural filler and silanated glass flakes. Advantageously, the uncured dental composition may have excellent handling properties based on thixotropic behaviour. Furthermore, the uncured dental composition may also have excellent handling properties in terms of an advantageous extrusion force for extruding the uncured dental composition through a nozzle.

DETAILED DESCRIPTION OF PREFERRED EMBODIMENTS

The terms "polymerization" and "polymerizable" relates to the combining or the capability to combine by covalent bonding of a large number of compounds such as smaller molecules, for example monomers, to form larger molecules, that is, macromolecules or polymers. The polymerizable compounds may be combined to form only linear macromolecules or they may be combined to form three-dimensional macromolecules, commonly referred to as crosslinked polymers. For example, monofunctional polymerizable compounds form linear polymers, whereas polymerizable compounds having at least two functional groups form crosslinked polymers also known as polymer networks. In case of a higher conversion rate of the polymerizable compounds, the amount of multifunctional polymerizable compounds may be reduced or the leaching problem may be alleviated.

The terms "curing" and "photocuring" mean the polymerization of functional polymerizable compounds such as monomers, oligomers or even polymers, into a crosslinked polymer network. Curing is the polymerization of unsaturated polymerizable compounds in the presence of cross-linking agents.

"Actinic radiation" is any electromagnetic radiation that is capable of producing photochemical action and can have a wavelength of at least 150 nm and up to and including 1250 nm, and typically at least 300 nm and up to and including 750 nm.

The term "photoinitiator" is any chemical compound that forms free radicals when activated, e. g. by exposure to light or interaction with a coinitiator in a photochemical process.

The term "coinitiator" refers to a molecule that produces a chemical change in another molecule such as a photoinitiator in a photochemical process. The coinitiator may be a photoinitiator or an electron donor.

The term "electron donor" as used herein means a compound which is capable of donating electrons in a photochemical process. Suitable examples include organic compounds having heteroatoms with electron lone pairs, for example amine compounds.

The term "structural filler" as used herein means any dental filler other than the silanated glass flakes (B) or the further filler (C) described below. Preferably, the structural filler is a dental glass, most preferably a dental glass selected from inert glasses, reactive glasses and fluoride releasing glasses.

The term "average particle size" as used herein in connection with the structural filler (A) refers to the arithmetic mean diameter of a particle and may be determined by any suitable means, such as light transmission or high resolution scanning electron microscopy.

The term "inert glass(es)" refers to a glass which is not capable of reacting with a polymer containing acidic groups in a cement reaction. Inert glasses are for example described in the Journal of Dental Research Jun. 1979, pages 1607-1619, or more recently in U.S. Pat. Nos. 4,814,362, 5,318, 929, 5,360,770, and application US 2004/0079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "reactive glass(es)" refers to a glass which is capable of reacting with a polymer containing acidic groups in a cement reaction. The glass is in particulate form. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

The term "fluoride releasing glass(es)" refers to a glass capable to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

The term "sphericity" as used herein means the ratio of the surface area of a sphere with the same volume as the given particle in the form of structural filler (A) to the surface area of the particle in the form of a structural filler (A).

The term "flake" as used herein means that the glass is in the form of a flake, that is its long diameter is larger than its thickness, at least by factor 2. The ratio of average long diameter to average thickness is termed "average aspect ratio" herein.

The term "silanated" as used herein means that the silanated glass flakes have silane coupling agent(s) on their surface, for example in the form of a coating at least partly and preferably fully covering the surface of the silanated glass flakes (B). The "silane coupling agent" may be any organosilane having one or more polymerizable groups and one or more hydolyzable groups, such as (meth)acryl or vinyl, for example 3-methacryloyloxy trimethoxysilane, vinyltrichlorosilane, tris (2-methoxyethoxy)-vinylsilane or tris (acetoxy)-vinylsilane.

The "average thickness" as used herein may be determined as follows: The thicknesses of 100 or more glass flakes of a sample are determined by scanning electron microscopy (SEM). Then, the total of the measured thicknesses is divided by the number of glass flakes for which the thickness was determined.

The term "gloss" as used herein means the optical property indicating how good or bad a surface reflects light in a specular direction. Gloss is affected by the refractive index of the material, the angle of incident light and the surface topography. Apparent gloss depends on the amount of specular reflection, that is light reflected from the surface in an equal amount and the symmetrical angle to the one of incoming light. The specular reflection can be calculated by the Fresnel equation, which is well known in the field of optics. Surface roughness in micrometer range influences the specular reflection levels. A low intensity of specularly reflected light means the surface is rough and it scatters the light in other directions. Specifically, a totally nonreflective surface has zero gloss units (G.U.), while a perfect mirror would have 1000 G.U. at a measuring angle of 60°. Typically, for gloss measurement, a measuring angle of 60° is applied, since this angle is considered to be the best angle to use so as to provide the closest correlation to a visual observation. 10 G.U. or less means low gloss, 10 to 70 G.U. are considered as semigloss, and a gloss >70 G.U. is considered as high gloss. For dental restorations prepared from the cured dental composition according to the present invention, semigloss (10 to 70 G.U.) and high gloss (>70 G.U.) are preferred, wherein high gloss is particularly preferred.

The specific selection of the silanized glass flakes (B) provides not only improved initial gloss, but also renders possible gloss retention for a relatively long period of time.

The term "gloss retention" as used herein means that the cured dental composition retains its initial gloss for a relatively long period of time, even when exposed to processing by a material removal method such as sanding or polishing, or likewise when the cured dental composition is exposed to typical daily loads such as tooth brushing, saliva fluid in the oral cavity and teeth grinding or clenching by the patient. It is readily understood that the planar, overlapping alignment of the glass flakes is more stable to the aforementioned loads, because in this arrangement, it is less likely that glass flake particles are removed by a mechanical load. That is, the surface of the cured dental composition will stay smooth for a relatively long time. Furthermore, regarding chemical resistance, for example in view of saliva fluid and/or acids from food, the planar, overlapping alignment of the glass flakes forms a kind of barrier which protects the cured dental composition as well as the tooth behind it from degradation by chemical influences such as acidity.

The present invention provides a dental composition being polymerizable or copolymerizable by any suitable kind of polymerization, preferably polymerization which can be initiated by an initiator system in the form of a photoinitiator system and/or a redox initiator system.

The dental composition may be a dental material to be used in the oral cavity. Preferably, the dental composition according to the invention is a dental composite or a dental cement.

The Structural Dental Filler (i)

The dental composition according to the present invention comprises a dental filler containing (A) a structural filler. The dental filler (i) may contain one or more fillers (A).

The structural filler (A) has an average particle size of from 0.1 to 3 μm. Preferably, the structural filler (A) has an average particle size of 0.2 to 2 μm, more preferably from 0.3 to 1.5 μm, most preferably from 0.5 to 1.2 μm. When the average particle size of the structural filler (A) is less than 0.1 μm, then the handling properties of the dental composition may deteriorate. When the average particle size of the structural filler (A) is more than 3.0 μm, then the gloss properties of the cured dental composition may deteriorate.

Preferably, the structural filler (A) is a reactive glass or a fluoride releasing glass. Most preferably, the structural filler (A) is a reactive glass.

Preferably, the dental composition contains the structural filler in an amount of 0.5 to 60 percent by weight, preferably 1 to 50 percent by weight, more preferably 3 to 40 percent by weight based on the total weight of the composition.

The structural filler (A) preferably has a sphericity of at least 0.5, more preferably at least 0.9, and most preferably at least 0.95.

Preferably, the structural filler (A) is silanated, more preferably silanated with an organosilane as described below for the silanated glass flakes (B).

The dental composition according to the present invention comprises a dental filler further containing silanated glass flakes (B). The dental filler (i) may contain one or more silanated glass flake fillers (B).

The silanated glass flakes (B) have (a) an average thickness between 50 nm and 1000 nm, and (b) an average aspect ratio (long diameter/thickness) in the range of from 2:1 to 50:1. While the above described average thickness of the silanated glass flakes (B) is from 50 to 1000 µm, the amount by weight of fractions of silanated glass flakes (B) having different thickness may vary in a sample, wherein preferably, the silanated glass flakes (B) include a fraction of silanated glass flakes having a thickness of 30 nm to 1500 nm, more preferably a thickness of 40 nm to 1000 nm, in an amount of at least 90% by weight.

Owing to the specific selection of average thickness and average aspect ratio of the silanized glass flakes (B), excellent gloss and gloss retention can be obtained and ensured for a long period of time. According to the present invention, self-alignment of the silanized glass flakes (B) within the polymer matrix of cured dental composition is possible, whereby the glass flakes may arrange by partially overlapping. Planar and overlapping self alignment provides a smooth surface of the cured dental composition. Therefore, the dental composition will have an improved initial gloss compared to conventional composition containing glass in the form of spheres or fibers.

In addition, the silanated glass flakes (B) may provide for an advantageous viscosity of the uncured dental composition. In particular, the silanated glass flakes (B) may provide for a thixotropic behaviour of the dental composition.

According to the present invention, the combination of structural filler (A) and silanated glass flakes (B) is suitable for adjusting the viscosity of the dental composition within a desired range. The silanated glass flakes (B) may also be advantageous in terms of the mechanical properties and long-term mechanical resistance of the cured dental composition as they impart isotropic reinforcement due to their high aspect ratio and due to to the advantageous arrangement in the form of planar, overlapping alignment of the glass flakes, which arrangement may provide for uniform reinforcement and increased dimensional stability.

The combination of the silanated glass flakes (B) and the structural filler (A) is specifically selected in order to attain well balanced properties for the cured dental composition. Owing to the specific combination of silanated glass flakes (B) and the structural filler (A), excellent gloss, gloss retention and long-term chemical resistance may be attained as well as excellent mechanical properties and long-term mechanical resistance. The small, nano-sized silanated glass flakes (B) readily arrange between and around the structural filler (A) which may be considerable larger with up to 3 µm. Thereby, the small, nano-sized silanated glass flakes (B) may self-align in the form of the above described planar, overlapping alignment, which may provide for a kind of barrier or shield effect. That is, the large structural filler (A) particles are prevented from being removed from the cured dental composition by mechanical forces or chemical influences, since they are shielded by the planar, overlapping alignment of the silanated glass flakes (B). As a result of this shielding, instead of a large structural filler (A), at best, if that, the small, nano-sized silanated glass flakes (B) are removed from the cured dental composition. Owing to this shield effect, an excellent gloss retention is attained, since after removal of a small particle, the surface of the cured dental composition will still be smooth and have an excellent gloss compared to a cured composition from which a large particle is removed, which results in a significantly irregular surface having a significantly deteriorated gloss. Furthermore, it is feasible that the glass flakes barrier properties also provide for both a good mechanical and chemical resistance due to a reduction of permeation rates of aggressive chemical, such as acidic fluids, into the large particle, which infiltration may result in removal of the particle when a mechanical force is applied, whereby gloss and long-term mechanical resistance is deteriorated.

Preferably, the structural filler (A) has an average particle size of from 0.3 to 2, more preferably of from 0.4 to 1.2.

Besides of the structural filler (A), the dental filler (i) contains (B) silanated glass flakes. The dental filler (i) may contain one or a mixture of two or more silanated glass flakes (B).

It was surprisingly found that owing to a certain ratio of the silaned glass flakes (B) and the structural filler (A), an uncured dental composition was obtained having a particularly advantageous extrusion force of below 70 N when extruding the uncured dental composition through a nozzle having a diameter typical for dental applications, for example a nozzle diameter of 1.2 to 2.4 mm, preferably 1.5 to 2.1 mm, most preferably 1.8 mm. Furthermore, the cured dental composition had advantageous mechanical properties such as a flexural strength of at least about 150 MPa, preferably 150 to 180 MPa, and an E-modulus of at least 11 GPa, preferably 11 to 14 GPa. As a result, the uncured dental composition can be easily applied owing to the advantageous extrusion force, and the cured composition exhibits mechanical properties providing for high mechanical resistance of the cured dental composition, for example against masticatory forces.

For silanated glass flakes (B), it is preferred that they have an average thickness between 80 nm and 1000 nm, more preferably between 100 nm and 450 nm, and most preferably between 120 nm and 400 nm.

Most preferably, the structural filler (A) has an average particle size of from 0.4 to 1.2, and the silanated glass flakes (B) have (a) an average thickness between 50 nm and 1000 nm, and (b) an average aspect ratio (long diameter/thickness) in the range of from 2:1 to 50:1.

The glass of the silanated glass flakes (B) preferably comprises the following components as oxides in percent by weight:

$SiO_2$=64-70
$B_2O_3$=2-5
$ZnO$=1-5
$Na_2O$=8-13
$MgO$=1-4
$CaO$=3-7
$Al_2O_3$=3-6,
and up to 3 percent of $K_2O$ and $TiO_2$.

The glass of the silanated glass flakes (B) is preferably an inert glass, wherein the term "inert glass" has the same meaning as described above for the structural filler (A).

The silanated glass flakes (B) are preferably obtainable by milling glass flakes having an aspect ratio of at least 20:1, and subsequently silanating the milled glass flakes. The milling of the glass flakes is not particularly limited and may be carried out with any apparatus typically applied for milling dental filler materials, such as a ball milling apparatus, or a pearl mill apparatus.

The particle size of the milled glass flakes prior to silanation may for example be suitable set by milling conditions selected from average particle size of the glass flakes used as starting material, grinding time, as well as amount, size and material of the grinding material such as balls or pearls and fluid such as water.

For example, for milling, as a starting material, glass flakes may be used which have an average particle size determined by light scattering of less than 700 µm, more preferably 40 to 500 µm, and most preferably 50 to 300 µm. It is preferred that the particle size distribution of the starting material is such that at least 50 percent of the particles have the aforementioned average particle size, more preferably at least 60 percent, even more preferably at least 65 percent. Most preferably, the starting material has a particle size distribution determined by light scattering, wherein at least 65 percent of the particles have a particle size of 50 to 300 µm.

It was surprisingly found that by setting the average particle size distribution of the milled glass flakes prior to silanation the extrusion force for extruding the uncured dental composition according to the invention through a nozzle can be advantageously set within the range of about 40 to 120 N. In addition, the cured dental composition has advantageous mechanical properties such as a flexural strength of about of 150 to 180 MPa and E-modulus of about 11 to 14 GPa.

Specifically, it was found that the desirable extrusion force was obtained when the milled glass flakes have a volume-based average particle size distribution (d3,50) determined by light scattering, wherein at least 50 percent of the particles have a particle size of 7 to 50 µm, more preferably 8 to 40 µm, most preferably 10 to 30 µm.

The term "particle size" as used in connection with the glass flakes used as starting material for milling and the milled glass flakes means the particle size diameter of the glass flakes.

The thus obtained milled glass flakes may be silanated with a silane having one or more polymerizable groups reactive with the polymerizable compounds (ii). Silanes for silanating filler materials of dental compositions are well known and a large variety thereof for dental applications is described for example by J. M. Antonucci, Journal of Research of the National Institute of Standards and Technology, 2005, vol. 110, no. 5, pages 541 to 558.

Typically, organosilanes of formula (I)

$(R_1,R_2,R_3)Si(R_H)_n$           (I)

are applied, wherein n is 1 to 3 and the number of substituents $R_1$, $R_2$, $R_3$ is 4–n, wherein at least one of $R_1$, $R_2$, $R_3$ represents a polymerizable group. $R_H$, which may be the same or different if two or three groups $R_H$ are present, represent(s) a hydrolysable group capable of reacting with the surface of the filler material to be coated. $R_H$ may be selected from the group consisting of alkoxy groups, ester groups, halogen atoms and amino group, wherein the alkoxy groups are preferably linear $C_{1-8}$ or branched or cyclic $C_{3-8}$ alkoxy groups, and the ester groups are preferably carboxylates having linear $C_{1-8}$ or branched or cyclic $C_{3-8}$ alkyl groups. Most preferably, the hydrolysable group $R_H$ represents an alkoxy group.

The groups $R_1$, $R_2$ and $R_3$ may be the same or different and represent unreactive groups and/or polymerizable groups, with the proviso that at least one of $R_1$, $R_2$ and $R_3$ represents a polymerizable group. Unreactive groups for $R_1$, $R_2$ and $R_3$ may be represented by alkyl groups, preferably linear $C_{1-8}$ or branched or cyclic $C_{3-8}$ alkyl groups. Polymerizable groups for $R_1$, $R_2$ and $R_3$ are preferably selected from the group consisting of a (meth)acryl group, a vinyl group or an oxirane group, more preferably (meth)acryl group or a vinyl group, and most preferably a (meth)acryl group which may be in the form of e.g. methacryloxy or methacryloxyalkyl wherein alkyl means a linear $C_{1-8}$ or branched or cyclic $C_{3-8}$ alkyl group.

Particularly preferred organosilanes are for example 3-methacryloxy trimethoxysilane, vinyltrichlorosilane, tris (2-methoxyethoxy)-vinylsilane or tris(acetoxy)-vinylsilane, or any one of the specific group of organosilanes disclosed in EP 0969789 A1, namely 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyl-dichloromonomethyl-silane, 3-methacryloxypropylmonochlorodimethylsilane and 3-(trimethoxysilyl)propyl methacrylate.

Most preferably, the organosilane of formula (I) is 3-(trimethoxysilyl)propyl methacrylate.

Alternatively or additionally to the organosilanes of formula (I), so-called dipodal organosilanes may be applied. Dipodal organosilanes are typically compounds of formula (II)

$((R_H)_3Si-R_4)_2CH-R_1$           (II), wherein $R_1$ and $R_H$ have the same meaning as defined above for the organosilane of formula (I), and $R_4$ represents an alkylene group, preferably a linear $C_{1-8}$ or branched or cyclic $C_{3-8}$ alkylene group.

The silanated glass flakes (B) preferably have a particle size distribution determined by light scattering, wherein at least 70 percent, more preferably at least 75 percent, even more preferably at least 80 percent of the particles have a particle size of less than 50 µm, yet even more preferably at least 80 percent of the particles have a particle size of 8.5 to 40 µm, and most preferably at least 80 percent of the particles have a particle size of 11 to 35 µm.

It is particularly preferred that the silanated glass flakes (B) preferably have a volume-based average particle size distribution (d3,50) determined by light scattering, wherein at least 50 percent of the particles have a particle size of 8.5 to 40 µm, most preferably 11 to 35 µm.

The term "particle size" as used in connection with the silanated glass flakes (B) means the particle size diameter of the glass flakes.

It is preferred that the silanated glass flakes (B) have a refractive index in the range of 1.46 to 1.60.

The structural filler (A) and the silanated glass flakes (B) may be suitably selected, preferably by selecting a ratio of the average particle size of the structural filler (A) and the average thickness of the silanated glass flakes (B) within the range of 10:1 to 1:1, more preferably 7:1 to 1.2:1, most preferably 4:1 to 1.4:1.

Preferably, the dental composition contains the silanated glass flakes (B) in an amount of from 0.5 to 40 percent, more preferably 1 to 30 percent, even more preferably 10 to 25, or 3 to 20 percent by weight based on the total weight of the composition.

In the dental composition, the ratio of the weight of structural filler (A) and the weight of the silanated glass flakes (B) is preferably in the range of from 80:1 to 0.5:1, more preferably 40:1 to 1:1, even more preferably 20:1 to 1.5:1, yet even more preferably 10:1 to 2:1 and most preferably 5:1 to 2.5:1.

According to an alternative, particular preferred embodiment, in the dental composition, a ratio of the weight of the silanated glass flakes (B) to the weight of structural filler (A) is preferably 0.025 to 2:1, more preferably 0.05:1 to 1.5:1, even more preferably 0.075:1 to 1:1, yet even more preferably 0.1:1 to 0.75:1 and most preferably 0.125:1 to 0.6:1.

It was surprisingly found that owing to this alternative, particular preferred specific ratio of weight of the silanated glass flakes (B) to the weight of structural filler (A), an uncured dental composition was obtained having a particularly advantageous extrusion force of about 40 to 120 N for extruding the uncured dental composition through a nozzle having a diameter typical for dental applications, for example a nozzle diameter of 1.2 to 2.4 mm, preferably 1.5 to 2.1 mm, most preferably 1.8 mm. In addition, the cured dental composition has advantageous mechanical properties such as a flexural strength of about 110 to 180 MPa and E-modulus of about 9 to 14 GPa.

Hence, owing to this alternative, particular preferred specific ratio of weight of the silanated glass flakes (B) to the weight of structural filler (A), the present dental composition according to the invention provides an advantageous extrusion force from a nozzle in uncured form, as well as excellent mechanical properties in terms of flexural strength and E-modulus in cured form.

It is particularly preferred that the silanated glass flakes (B) have a particle size distribution determined by light scattering, wherein at least 80 percent of the particles have a particle size of 11 to 40 μm, and the ratio of the weight of the silanated glass flakes (B) to the weight of structural filler (A) is in the range of from 0.125:1 to 0.6:1.

It is preferred that the dental composition contains 1 to 85 percent by weight of the dental filler (i) based on the total weight of the composition.

The silanated glass flakes having (a) an average thickness between 50 nm and 1000 nm and (b) an average aspect ratio in the range of form 2:1 to 50:1 may be used for the preparation of a dental composition, preferably for the preparation of a dental composition as described above.

The One or More Polymerizable Compounds (ii)

Besides of the dental filler (i), the dental composition of the present invention may further contain (ii) one or more polymerizable compounds having at least one polymerizable group.

The term "polymerizable compounds" as used herein encompasses monomers, oligomers and polymers. Preferably, the one or more polymerizable compounds is/are monomers.

The polymerizable group of the further contained one or more polymerizable compounds (ii) is not particularly limited. The at least one polymerizable group may for example be a radically polymerizable carbon-carbon double bond and/or a cationically polymerizable group. Preferably, radically polymerizable carbon-carbon double bonds are selected from carbon-carbon double bonds of (meth)acryloyl group(s) and a (meth)acrylamide group, preferably (meth)acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

The one or more polymerizable compounds (ii) having at least one radically polymerizable carbon-carbon double bonds are not particularly limited. However, preferably, their radically polymerizable carbon-carbon double bonds are selected from carbon-carbon double bonds of a (meth) acryloyl group and a (meth)acrylamide group.

Suitable examples of polymerizable compounds (ii) having at least one radically polymerizable carbon-carbon double bonds may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

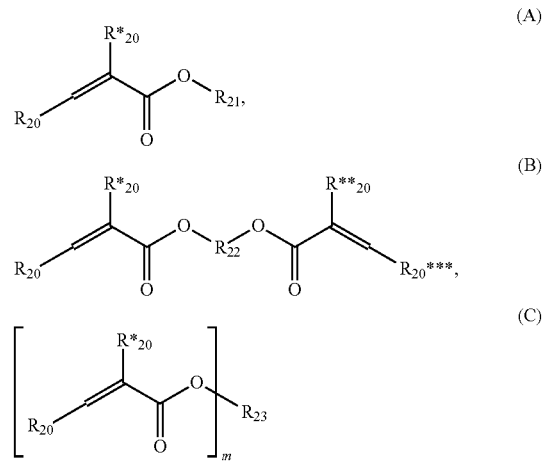

wherein $R_{20}$, $R^*_{20}$, $R^{}_{20}$, and $R^{*}_{20}$ independently represent a hydrogen atom, —COOM, a linear $C_{1-18}$ or branched $C_{3-18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, —COOM, —PO$_3$M, —O—PO$_3$M$_2$ or —SO$_3$M*, $R_{21}$ represents a hydrogen atom, a linear $C_{1-18}$ or branched $C_{3-18}$ alkyl group or $C_2$ and $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M*, or a $C_5$ to $C_{18}$ aryl or $C_3$ to $C_{18}$ heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—) or 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituents selected from the group consisting of a hydroxyl group, a thiol group, a $C_{6-14}$ aryl group, —COOM, —PO$_3$M, —O—PO$_3$M$_2$ or —SO$_3$M*; preferably $R_{22}$ is a $C_1$ to $C_{18}$ alkylene group or a $C_2$ to $C_{18}$ alkenylene group, which may be substituted by one or more —OH group(s), which alkylene or alkenylene group may contain at least one of 1 to 4 $C_{6-10}$ arylene groups, 1 to 4 urethane groups (—NH—(C=O)—O— or —O—(C=O)—NH—), and 1 to 8 oxygen atoms;

$R_{23}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one of $R_{20}$, $R^*_{20}$, $R^{}_{20}$, and $R^{*}_{20}$, $R_{21}$, and $R_{22}$, which M are independent from each other, each represent a hydrogen atom or a metal atom, and M* of any one of $R_{20}$, $R^*_{20}$, $R^{}_{20}$, and $R^{*}_{20}$, $R_{21}$, and $R_{22}$, which M are independent from each other, each represent a metal atom.

For $R_{20}$, $R^*_{20}$, $R^{}_{20}$, and $R^{*}_{20}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$ and $R^*_{21}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, and $R^{*}_{20}$ and $R_{21}$ an aryl group may, for example, be a phenyl group or a naphthyl group, and a $C_{3-14}$ heteroaryl group may contain 1 to 3 heteroatoms selected from nitrogen, oxygen and sulfur.

For $R_{22}$, in the phrase "divalent organic residue may contain at least one of . . . " means that the groups which may be contained in the divalent organic residue are incorporated in the divalent organic residue by means of covalent bonding. For example, in BisGMA, two aryl groups in the form of phenyl and two heteroatoms in the form of oxygen are incorporated into the divalent organic residue of $R_{22}$. Or, as a further example, in UDMA, two urethane groups (—NH—(C=O)—O— or —O—(C=O)—NH—) are incorporated in the divalent organic residue of $R_{22}$.

In formula (B), the dotted bond indicates that $R_{20}$ and $R^{***}_{20}$ may be in (Z) or (E) configuration relative to CO.

Preferably, in formulae (A), (B) and (C), $R_{20}$, $R^*_{20}$, $R^{}_{20}$ and $R^{*}_{20}$ independently represent a hydrogen atom, a linear $C_{1-16}$ or branched $C_{3-16}$ alkyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^*_{20}$, $R^{}_{20}$, and $R^{*}_{20}$ and $R^{***}_{20}$ independently represent a hydrogen atom, a linear $C_{1-8}$ or branched $C_{3-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{20}$, $R^*_{20}$, $R^{}_{20}$, and $R^{*}_{20}$ and $R^{***}_{20}$ independently represent a hydrogen atom, a linear $C_{1-4}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^*_{20}$, $R^{}_{20}$, and $R^{*}_{20}$ and $R^{***}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-16}$ alkenyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, $R_{21}$ represents a hydrogen atom, a linear $C_{1-10}$ or branched $C_{3-10}$ alkyl or $C_{2-10}$ alkenyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{21}$ represents is a hydrogen atom, a linear $C_{1-10}$ or branched $C_{3-10}$ alkyl group or linear $C_{2-10}$ or branched $C_{3-10}$ alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, still even more preferably an unsubstituted $C_{2-6}$ alkyl group or C3-6 alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylate ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4)_(UDMA), glycerol mono-and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2- methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)]propane, 2,2'-bis[4(2-hydroxy-3-acryloxy-phenyl) propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl) propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane.

Most preferably, a compound of formula (B) is selected from the group consisting of:

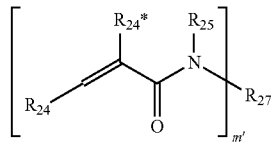
(F)

wherein $R_{24}$ $R^*_{24}$, $R^{}_{24}$, and $R^{*}_{24}$ have the same meaning as $R_{20}$ $R^*_{20}$, $R^{}_{20}$, $R^{*}_{20}$ defined above for formulae (A), (B) and (C), $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{6-14}$ arylene groups, from 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO$_3$M, —O—PO$_3$M$_2$ or —SO$_3$M* Preferably, $R_{26}$ is a $C_1$ to $C_{18}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or —O—(C=O)—NH—), and 1 to 8 oxygen atoms or nitrogen atoms.

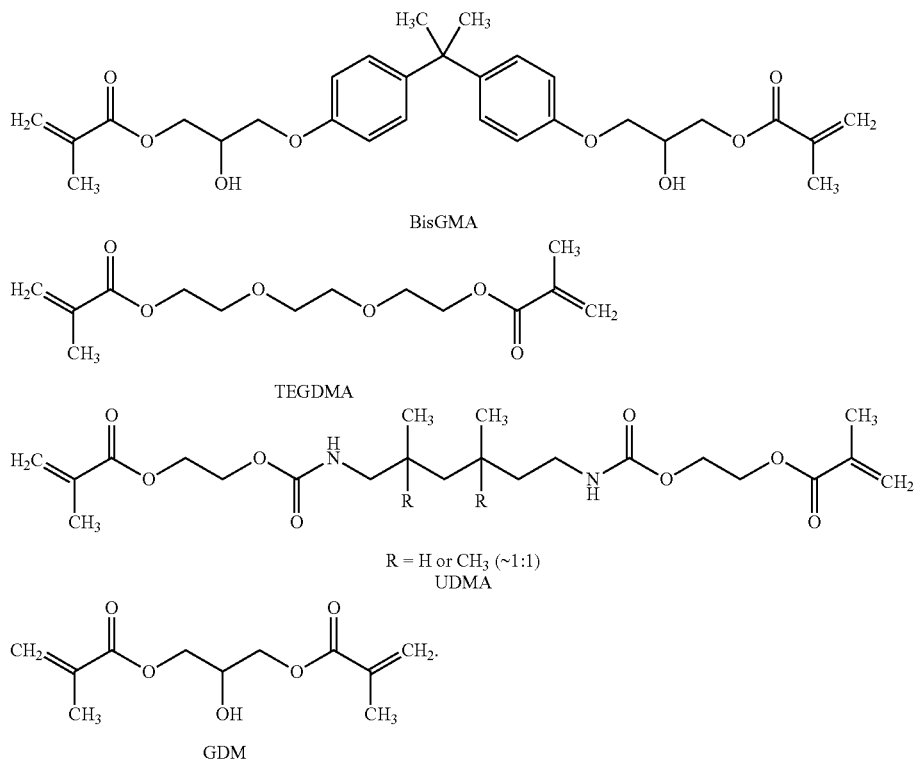

Particular preferred mono- or bis- or (meth)acrylamides and poly[(meth) acrylamides] have the following formulae (D), (E) and (F):

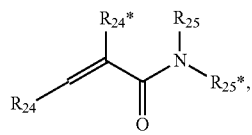
(D)

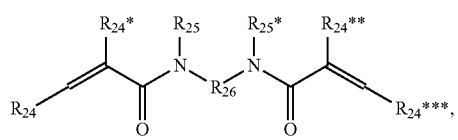
(E)

For $R_{26}$, the phrase "divalent organic residue may contain at least one of . . ." has an analogous meaning as defined above for $R_{22}$ of compound of formula (B).

In formulae (D), (E), (F), the dotted bond indicates that $R_{24}$ and $R^{***}_{24}$ may be in (Z) or (E) configuration relative to CO.

In compound of formula (D), $R_{25}$ and $R_{25}*$ may cooperatively form a ring in which $R_{25}$ and $R_{25}*$ are linked by a C—C bond or a functional group selected from the group consisting of an ether group, a thioether group, an amine group and an amide group.

Preferred methacrylamides according to formulae (D), (E), (F) have the following formulae:

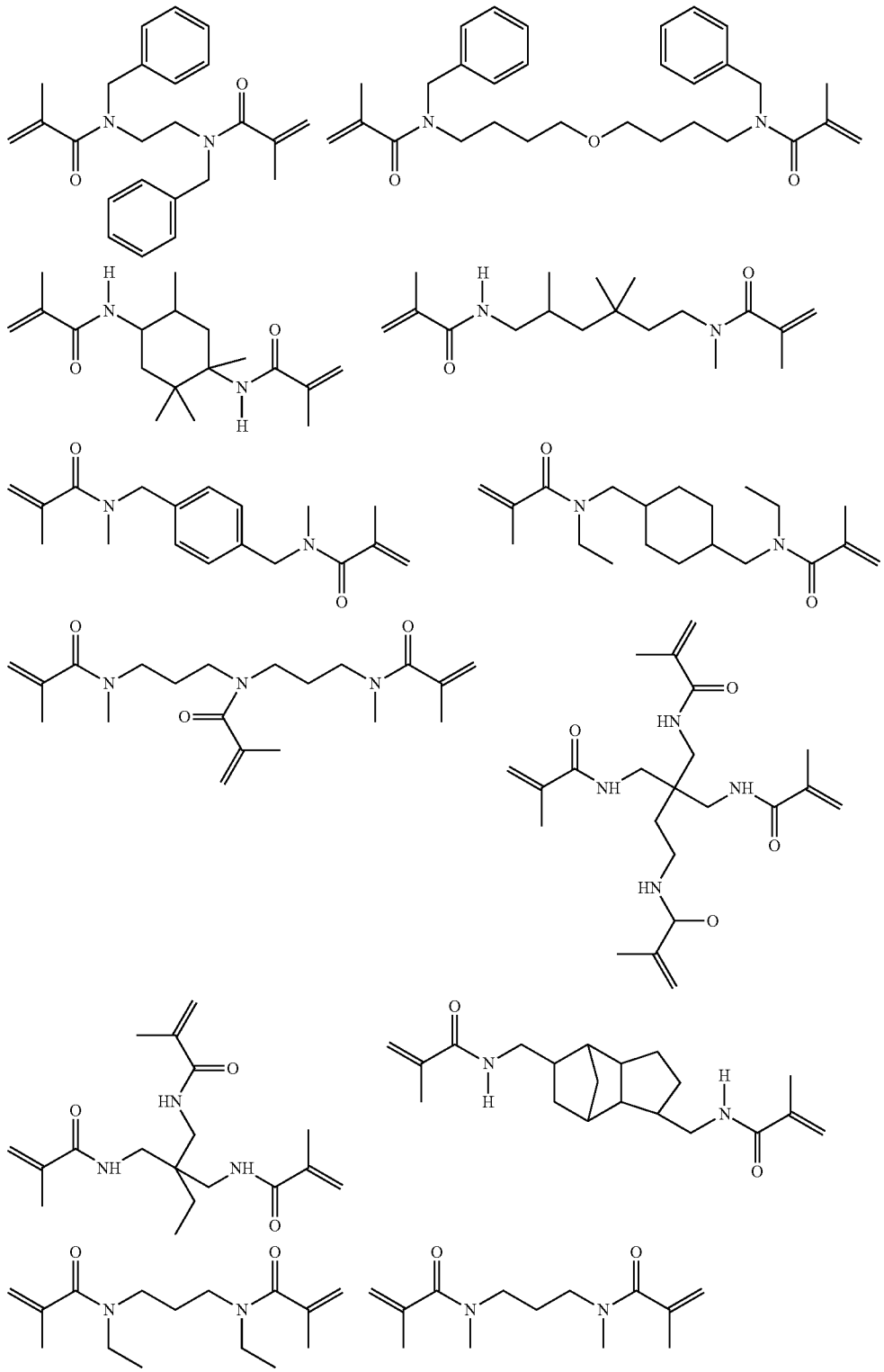

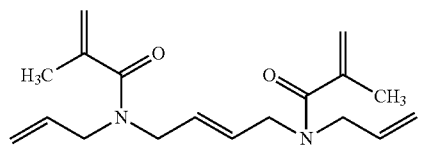
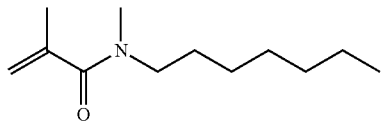
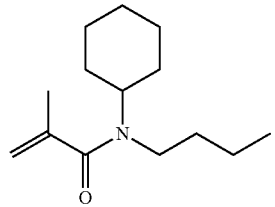
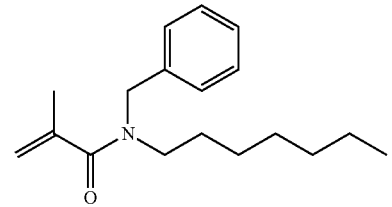
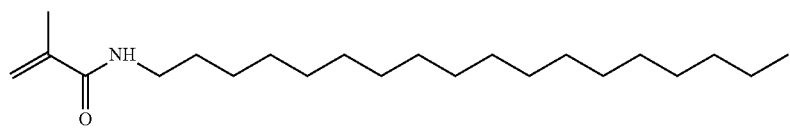
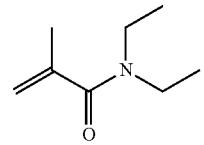
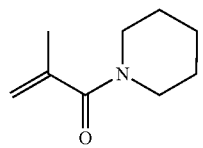
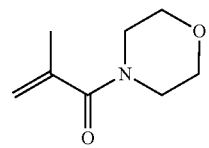
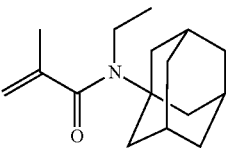
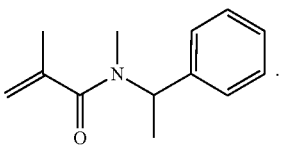
Preferred acrylamides according to formulae (D), (E), (F) have the following formulae:
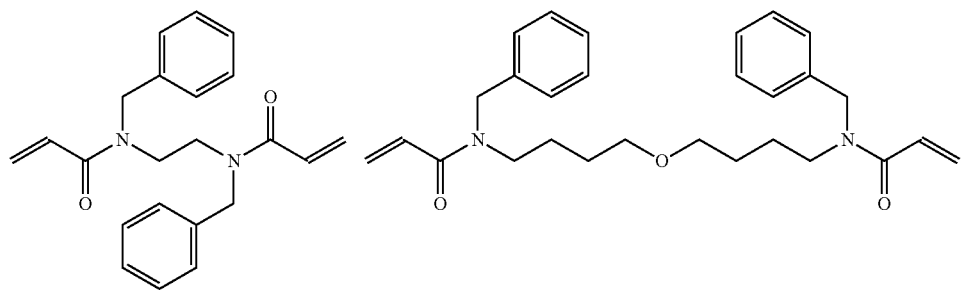
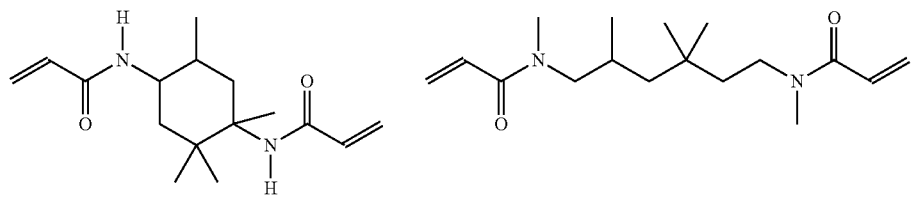
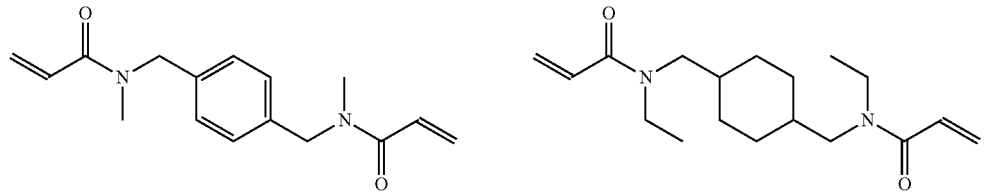

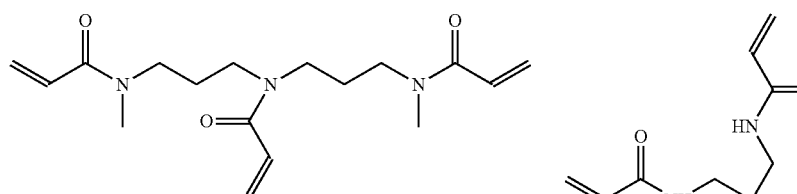
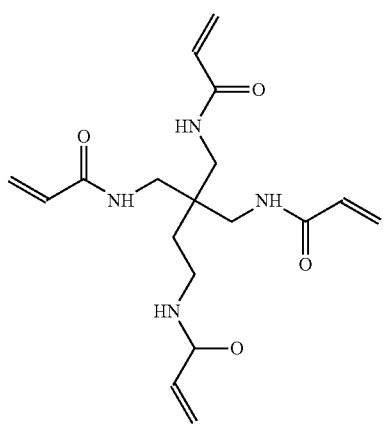
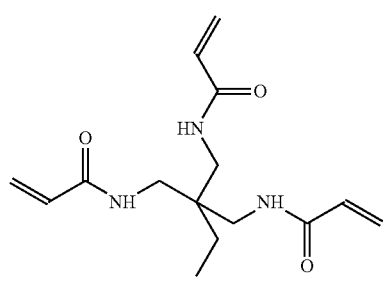
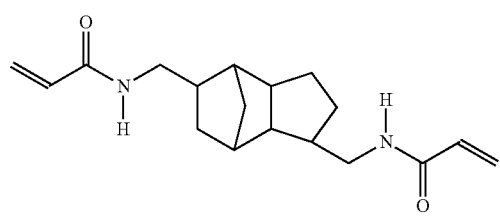
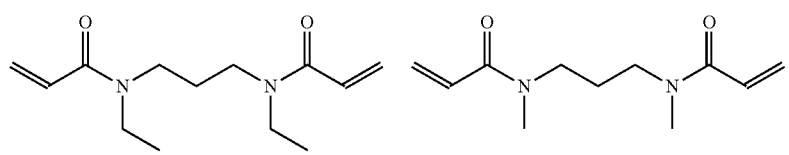
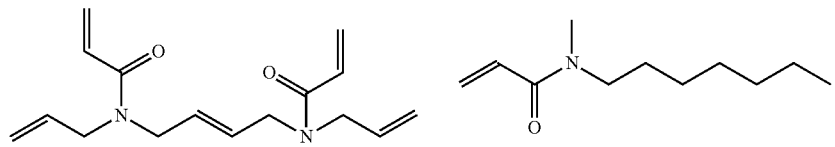
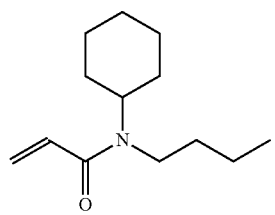
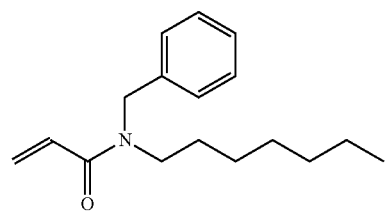
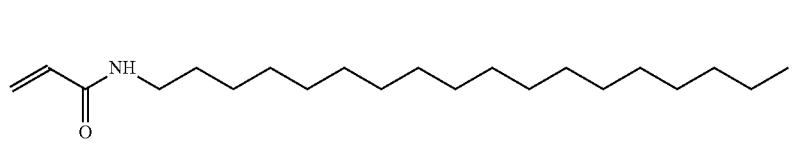
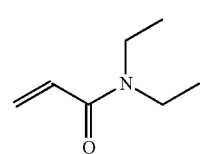
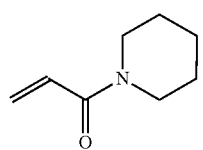
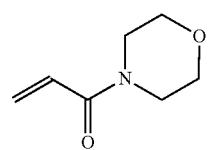
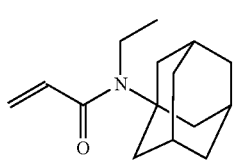
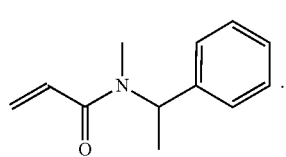

Most preferred are the bis-(meth)acrylamides:
N,N'-diallyl-1,4-bisacrylamido-(2E)-but-2-en (BAABE) having the structural formula

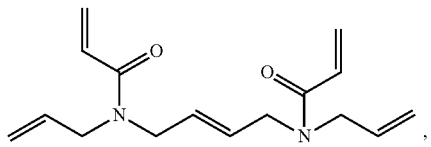 [SMILES: C=CCN(C/C=C/CN(CC=C)C(=O)C=C)C(=O)C=C]

and
N,N'-diethyl-1,3-bisacrylamido-propan (BADEP) having the structural formula

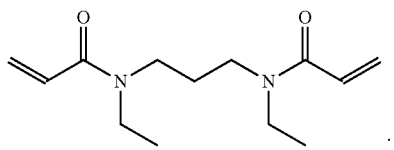 [SMILES: C=CC(=O)N(CC)CCCN(CC)C(=O)C=C]

Compounds having a (meth)acryloyl group or a (meth)acrylamide group may also preferably be selected from phosphoric acid ester group containing polymerizable monomers having at least one polymerizable double bond preferably have the following formula (G):

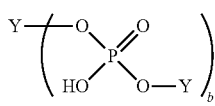
(G)

wherein
the moieties Y independent from each other represent a hydrogen atom or a moiety of the following formulae (Y*), (Y) or (Y*):

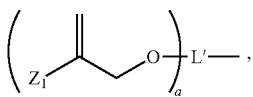
(Y*)

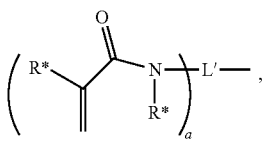
(Y**)

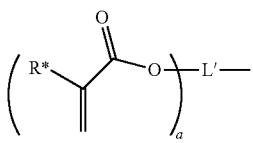
(Y***)

wherein
$Z_1$ is $COOR^\alpha$, $COSR^\beta$, $CON(R^\alpha)_2$, $CONR^\alpha R^\beta$, or $CONHR^\alpha$, wherein $R^\alpha$ and $R^\beta$ independently represent a hydrogen atom, a $C_{1-18}$ alkyl group optionally substituted by a $C_3$-8 cycloalkyl group, an optionally substituted $C_3$-8 cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{13}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

R■ and R● independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L* represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP 1 548 021 A1.

Furthermore, compounds having a (meth)acryloyl group or a (meth)acrylamide group may also be selected from phosphonic acid group containing polymerizable acidic compounds of the following formula (H):

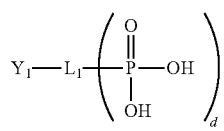
(H)

wherein
the moiety $Y_1$ represents a moiety of the following formulae ($Y_1$) or ($Y_1$*):

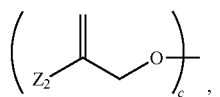
($Y_1$*)

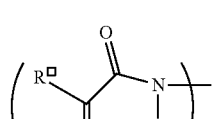
($Y_1$**)

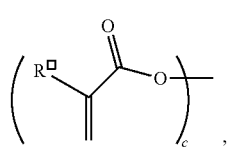
($Y_1$***)

$Z_2$ independently has the same meaning as defined for $Z_1$;

R$^\square$ and R$^\circ$ independently have the same meaning as defined for R$^\blacksquare$ and R$^\bullet$;

L$_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula (Y$_1$*), (Y$_1$) and (Y$_1$*); and c and d independently represent integers of from 1 to 10.

From compound of formula (G'), the following formulae are particularly preferred:

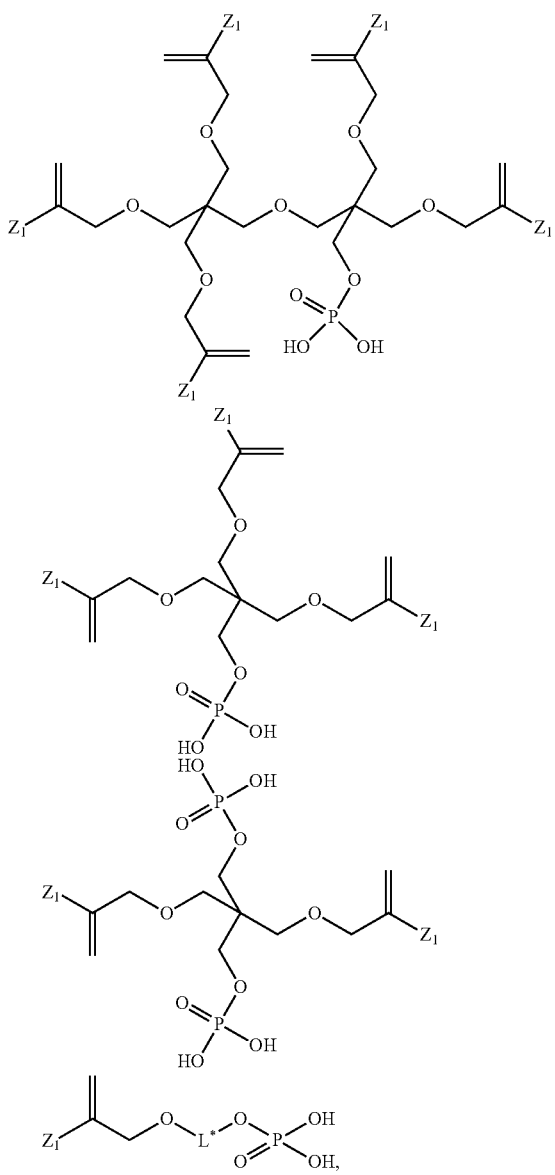

wherein Z$_1$ is defined as above, and L* is an optionally substituted alkylene group. More preferably, Z$_1$ is methyl, and L* is a C$_4$ to C$_{16}$ alkylene group. Even more preferably, L* is a C$_8$ to C$_{12}$ alkylene group.

Furthermore, compounds having one or more radically polymerizable carbon-carbon double bonds may be selected from the hydrolysis stable polyfunctional polymerizable monomers disclosed in EP 2 705 827 and EP 2 727 576.

Particularly preferred compounds having one or more radically polymerizable carbon-carbon double bonds are selected from the compounds of formulae (A), (B), (C), (G), (H), more preferably from the compound of formulae (A), (B), (C), and most preferably from compounds of formula (B).

The one or more polymerizable compounds (ii) having one or more cationically polymerizable groups are not particularly limited. However, preferably, their cationically polymerizable groups are selected from epoxide groups, oxetane groups, vinyl ether groups, aziridine groups, and azetidine groups, more preferably from epoxide groups, oxetane groups and vinyl ether groups, and most preferably from epoxide groups and vinyl ether groups.

A compound having one or more cationically polymerizable groups in the form of an epoxide and/or oxetane group may be preferably selected from the compounds of the formulae (J), (K), (L):

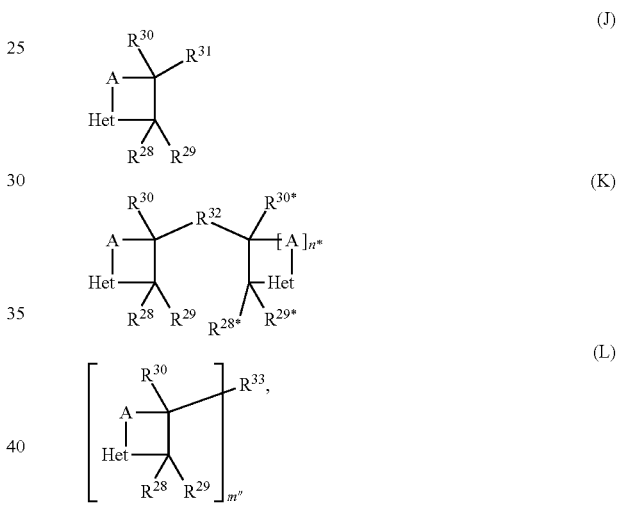

wherein

A is a single bond, a methylene (—CH$_2$—) group or a —R$^{28}$CR$^{29}$— in which R$^{28}$ and R$^{29}$ have the same meaning as defined below for R$^{28}$ and R$^{29}$, preferably A is a single bond or a methylene (—CH$_2$—) group, most preferably A is a single bond, Het is an oxygen atom or a nitrogen atom, preferably an oxygen atom, R$^{28}$, R$^{29}$, R$^{30}$, R$^{28*}$, R$^{29*}$, R$^{30*}$, R$^{31}$ independently represent a hydrogen atom, —COOM, an organic moiety selected from the group consisting of a linear C$_{1-18}$ or branched C$_{3-18}$ alkyl group which may be substituted by a C$_{3-6}$ cycloalkyl group, a C$_{6-14}$ aryl or C$_{3-14}$ heteroaryl group, —COOM, —PO$_3$M, —O—PO$_3$M$_2$ or —SO$_3$M*, a C$_3$ to C$_{18}$ cycloalkyl group which may be substituted by a linear C$_{1-16}$ or branched or cyclic C$_{3-16}$ alkyl group, a C$_{6-14}$ aryl or C$_{3-14}$ heteroaryl group, —COOM, —PO$_3$M, —O—PO$_3$M$_2$ or —SO$_3$M*, or a C$_5$ to C$_{18}$ aryl or C$_3$ to C$_{18}$ heteroaryl group which may be substituted by —COOM, —PO$_3$M, —O—PO$_3$M$_2$ or —SO$_3$M*, which organic moiety may be substituted with one or more substituent(s) selected from the group consisting of, $R^{32}$ represents a divalent organic residue having from 1 to 45 carbon atoms, whereby said organic residue may contain at least one of 1 to 7 $C_{3-12}$ cycloalkylene group(s), 1 to 7 $C_{6-14}$ arylene groups, 1 to 7 carbonyl groups, 1 to 7 carboxyl groups (—(C═O)—O— or —O—(C═O)—), 1 to 7 amide groups (—(C═O)—NH— or —NH—(C═O)—), 1 to 7 urethane groups (—NH—(C═O)—O— or —O—(C═O)—NH—), 1 to 14 heteroatoms selected from silicon, oxygen, nitrogen and sulphur; preferably $R^{32}$ is a $C_1$ to $C_{18}$ alkylene group which may contain at least one of 1 to 4 carboxyl groups (—(C═O)—O— or —O—C═O—)) or at least one moiety —SiR$^{\bullet}_2$—O—SiR$^{\bullet}_2$— wherein R$^{\bullet}$ independently represent a linear $C_{1-4}$ or branched $C_3$ or $C_4$ alkyl group, which divalent organic residue may be substituted with one or more group selected from the group consisting of —OH, —SH, —COOM, —PO$_3$M, —O—PO$_3$M$_2$ or —SO$_3$M*;

and $R^{33}$ represents a saturated di- or multivalent substituted or unsubstituted linear $C_1$ to $C_{18}$ hydrocarbon group, a saturated di- or multivalent substituted or unsubstituted branched or cyclic $C_3$ to $C_{18}$ hydrocarbon group, a di- or multivalent substituted or unsubstituted $C_6$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen or sulphur atoms, and m" is an integer, preferably in the range from 1 to 10, wherein M of any one $R^{28}$, $R^{29}$, $R^{30}$, $R^{28*}$, $R^{29*}$, $R^{30*}$, $R^{31}$ and $R^{32}$, which M are independent from each other, each represent a hydrogen atom or a metal atom, and M* of any one $R^{28}$, $R^{29}$, $R^{30}$, $R^{28*}$, $R^{29*}$, $R^{30*}$, $R^{31}$ and $R^{32}$, which M are independent from each other, each represent a metal atom.

In compound of formulae (J), (K) and (L), $R^{28}$, $R^{30}$ and $R^{28*}$, $R^{30*}$ independently may cooperatively form a ring in which $R^{28}$, $R^{30}$ and $R^{28*}$, $R^{30*}$ are linked by a C—C bond or a functional group selected from the group consisting of an ether group, a thioether group, an amine group and an amide group. Preferably, $R^{28}$, $R^{30}$ and $R^{28*}$, $R^{30*}$ are linked by a C—C bond and form, together with the C—C bond located between $R^{28}$, $R^{30}$ and $R^{28*}$, $R^{30*}$ a 3 to 8 membered ring, preferably a 5 to 7 membered ring, most preferably a $C_6$ ring.

For $R^{32}$, the phrase "divalent organic residue may contain at least one of . . . " has an analogous meaning as defined above for $R_{22}$ of compound of formula (B).

It is preferred that in formula (J), Het is oxygen, $R^{28}$ and $R^{29}$ independently represent a linear $C_{1-8}$ or branched or cyclic $C_{3-8}$ alkyl group which may be substituted with one or more —OH groups. More preferably, in formula (J), Het is oxygen, $R^{28}$ and $R^{29}$ independently represent a linear $C_{1-8}$ alkyl group which may be substituted with one or more —OH groups, and $R^{30}$ and $R^{31}$ represent hydrogen atoms, wherein A is preferably a methylene (—CH$_2$—) group.

It is preferred that in formula (K), A is a single bond, Het is oxygen, $R^{28}$, $R^{30}$ and $R^{28*}$, $R^{30*}$ independently cooperatively form a ring in which $R^{28}$, $R^{30}$ and $R^{28*}$, $R^{30*}$ are linked by a C—C bond, and $R^{32}$ is a $C_1$ to $C_8$ alkylene group which may contain at least one of 1 to 4 carboxyl groups (—(C═O)—O— or —O—(C═O)—)) or at least one moiety —SiR$^{\bullet}_2$—O—SiR$^{\bullet}_2$— wherein R$^{\bullet}$ independently represent a linear $C_{1-4}$ or branched $C_3$ or $C_4$ alkyl group.

Preferably, compounds of formulae (J) and (K) are selected from the group consisting of:

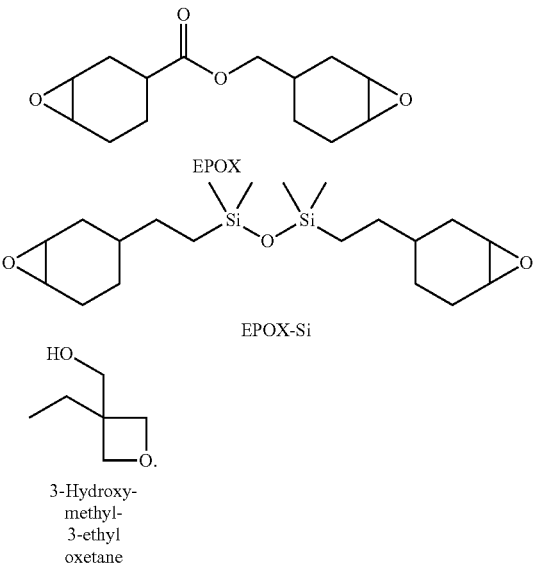

EPOX

EPOX-Si

3-Hydroxy-methyl-3-ethyl oxetane

Most preferred are compounds of formula (K) being EPDX and/or EPDX-Si.

A compound having one or more cationically polymerizable groups in the form of a vinyl ether group may be preferably selected from the compounds of the formulae (M), (N), (O):

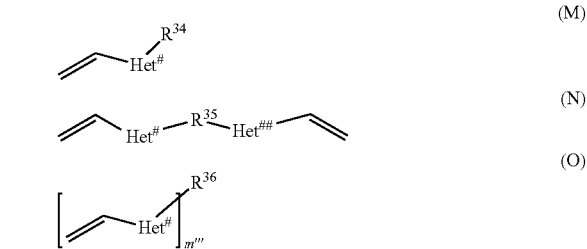

$R^{34}$ has the same meaning as $R^{21}$ defined above for formula (A) or may alternatively represent a monovalent substituted or unsubstituted $C_2$ to $C_{45}$ mono-, di-, or polyether residue having from 1 to 14 oxygen atoms, $R^{35}$ has the same meaning as $R^{22}$ defined above for formula (B), and $R^{36}$ and m'" have the same meaning as $R^{23}$ and m' as defined above for formula (C).

Preferably, in compound of formula (M), Het$^{\#}$ is an oxygen atom and $R^{34}$ represents a linear $C_{1-14}$ or branched or cyclic $C_{3-14}$ alkyl group, or an ethylenglycol moiety of formula —[—O—CH$_2$—CH$_2$—]$_n$—R$^y$ with n=1 to 9 and R$^y$ being hydrogen or OH.

Preferably, in compound of formula (N), Het$^{\#}$ and Het$^{\#\#}$ are oxygen atoms and $R^{35}$ represents a $C_1$ to $C_{18}$ alkylene group which may contain at least one of 1 to 4 $C_{3-8}$ cycloalkylene group or 1 to 9 oxygen atoms, wherein the oxygen atoms may be contained such that an ethylenglycol moiety of formula —[—O—CH$_2$—CH$_2$—]$_n$— with n=1 to 9 is formed.

Most preferably, compounds of formulae (M) and (N) are selected from the group consisting of:

Triethyleneglycol divinyl ether (DVE-3)

Di(ethylene glycol)vinylether (DEGVE)

1,4-Cyclohexanedimethanol divinyl ether (CHDVE)

DODECYL VINYL ETHER

Di(ethylene glycol) divinyl ether (DEGDVE)

Particularly preferred compounds having one or more cationically polymerizable groups are selected from the compounds of formulae (J), (K), (M) and (N), more preferably from the compounds of formulae (K), (M) and (N).

The one or more polymerizable compounds (ii) having a combination of at least one radically polymerizable carbon-carbon double bonds and at least one cationically polymerizable group(s) is not particularly limited. However, preferably, in such compound, the radically polymerizable carbon-carbon bonds are selected from (meth)acryloyl group(s) and (meth)acrylamide group(s), and the cationically polymerizable groups are selected from epoxide groups, oxetane groups, vinyl ether groups, aziridine groups, and azetidine groups. More preferably, in such compound, the radically polymerizable carbon-carbon bond(s) is/are (meth)acrylamide group(s), and the cationically polymerizable groups are selected from vinyl ether groups, epoxide groups and oxetane groups. Most preferably, the cationically polymerizable group(s) is/are vinyl ether group(s) and/or epoxide group(s).

A compound having a combination of at least one radically polymerizable carbon-carbon double bonds and at least one cationically polymerizable group(s) may preferably be selected from the compounds of formula (P):

(P)

$R^{37}$, $R^{38}$, $R^{39}$ have the same meaning as $R^{28}$, $R^{29}$, $R^{30}$ defined above for formulae (J), (K) and (L), $R^{40}$, $R^{40*}$ have the same meaning as $R_{20}$ and $R_{20}*$ defined above for formulae (A), (B) and (C), $R^{41}$ has the same meaning as $R_{23}$ defined above for formula (C), j is an integer of 0 to 6, preferably 1 to 3,
k is an integer of 0 to 6, preferably 0 to 3,
j is an integer of 0 to 6, preferably 0 to 3,
with the proviso that j+k+l≥2.

In formula (P), the dotted bond indicates that $R^{40}$ may be in (Z) or (E) configuration relative to CO.

In formula (P), $R^{37}$ and $R^{39}$ may cooperatively form a ring as defined above for $R^{28}$ and $R^{30}$ of formulae (G) and (H).

Most preferably, in compound (P), the radically polymerizable carbon-carbon bond(s) is/are (meth)acrylamide group(s), and the cationically polymerizable groups are vinyl ether groups.

It is preferred that in compound of formula (P), j=1 to 3, k=0 and j=1 to 3, $R^{40}$ is a hydrogen atom, $R^{40*}$ is a linear $C_{1-8}$ or branched or cyclic $C_{3-8}$ alkyl group, $R^{41}$ represents a $C_1$ to $C_{18}$ alkylene group which may contain 1 to 9 oxygen atoms, wherein the oxygen atoms may be contained such that an ethylene glycol moiety of formula —[—O—CH$_2$—CH$_2$—]$_n$— with n=1 to 9 is formed.

A particularly preferred compound of formula (P) is 2-vinyloxyethoxyethyl methacrylate (VEEM) having the following structural formula:

Preferably, the dental composition comprises a homogeneous phase comprising monomer combinations (x) and (y), (x) and (z), (y) and (z), or (x), (y) and (z), or comprising monomer (z), wherein (x) represents one or more compounds having at least one radically polymerizable carbon-carbon double bond;
(y) represents one or more compounds having at least one cationically polymerizable group;
(z) represents one or more compounds having a combination of at least one radically polymerizable carbon-carbon double bond and at least one cationically polymerizable group.

The term "homogeneous phase" means that monomer combinations (x) and (y), (x) and (z), (y) and (z), or (x), (y) and (z), or monomer(s) (z) are present in a single phase without detectable phase boundaries within the single phase.

The term "monomer(s)" as used herein means a compound having a polymerizable group.

The term "interpenetrating polymer network (IPN)" as used herein means that two or more polymers are at least partially interlaced on a molecular scale, but not covalently bonded to each other and cannot be separated unless chemical bonds are broken. A mixture of two or more pre-formed polymers does not represent an IPN. If the two or more polymers of the IPN are formed of compounds having two or more polymerizable groups, then the IPN is according to the official IUPAC definition: "a polymer comprising two or more networks which are at least partially interlaced on a molecular scale, but not covalently bonded to each other and cannot be separated unless chemical bonds are broken". If one or more polymer(s) is/are formed of a compound having two or more polymerizable groups, and one or more polymer(s) is/are formed of a compound having a single polymerizable group, then the IPN is, according to the IUPAC definition, a so-called "semi-interpenetrating polymer network (SIPN): "a polymer comprising on or more networks and one or more linear or branched polymer(s) characterized by the penetration on a molecular scale of at least one of the networks by at least some of the linear of branched macromolecules". The present general definition of IPN includes the IPNs and SIPNs according to IUPAC definition, but also two or more linear or branched polymers which are at least partially interlaced on a molecular scale, but not covalently bonded to each other, and which cannot be separated unless chemical bonds are broken.

The radically polymerizable carbon-carbon double bonds and cationically polymerizable groups of monomers (x), (y) and (z) are not particularly limited. Preferably, radically polymerizable carbon-carbon double bonds are selected from carbon-carbon double bonds of (meth)acryloyl group(s) and a (meth)acrylamide group(s), preferably (meth) acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

Preferably, the dental composition comprises a homogeneous phase comprising monomer combinations (x) and (y), (x) and (z), (y) and (z), or (x), (y) and (z), most preferably monomer combinations (x) and (y), (x) and (z), or (x), (y) and (z).

For example, monomer(s) (x) may be selected from compounds of formula (A), (B), (C), (D), (E), (F), (G) and (H), monomer(s) (y) may be selected from compounds of formula (J), (K), (L), (M), (N), (O), and monomer(s) (z) may be selected from compounds of formula (P).

Preferably, the homogeneous phase comprises one or more compound(s) (x) and/or (y) having two or more polymerizable carbon-carbon double bonds or cationically polymerizable groups, and/or one or more compound(s) (z) having at least one polymerizable carbon-carbon double bonds and at least one cationically polymerizable groups. This provides for the formation of a crosslinked polymer network. The formation of a crosslinked polymer network is advantageous, since it imparts additional dimensional/mechanical stability to the IPN formed. More preferably, the homogeneous phase (a) comprises compound(s) (x) having two or more radically polymerizable carbon-carbon bonds selected from the group consisting of compounds of formulae (B) and (E), and/or compound(s) (y) having two or more cationically polymerizable groups selected from the group consisting of compounds of formulae (K) and (O), and/or compound(s) (z) having at least one radically polymerizable carbon-carbon double bond and at least one cationically polymerizable group selected from compounds of formula (P).

For a homogeneous phase comprising compound(s) (x), it is preferred that the homogeneous phase (a) contains components (x), (y) and (z) in a weight ratio (x)/((y)+(z)) of from 0.1 to 10.

The Initiator System (iii)

The dental composition according to the present invention comprises an initiator system (iii). As a initiator system (iii), any compound or system capable of initiating the polymerization of the one or more polymerizable compounds (ii) may be used. The initiator system according to (iii) may be a photoinitiator system, a redox initiator system or a dual cure initiator system.

The term "dual cure initiator system" means an initiator system that contains a photoinitiator system and a redox initiator system.

For example, a suitable photoinitiator system may be in the form of a binary or tertiary system. A binary system may include a photoinitiator and an electron donor compound, and a tertiary system may include an iodonium, sulfonium or phosphonium salt, a photoinitiator, and an electron donor compound, as for example described in U.S. Pat. No. 5,545,676.

Suitable photoinitiators for the initiator system (iii) are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

A suitable photoinitiator system may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

Apart from the above mentioned photoinitiators, photoinitiators may be applied having the following formula (III):

$$X^P\text{—}R^P \quad (III)$$

wherein
$X^P$ is a group of the following formula (IV):

(IV)

wherein
M is Si or Ge;
$R^6$ represents a substituted or unsubstituted hydrocarbyl or hydrocarbylcarbonyl group;
$R^7$ represents a substituted or unsubstituted hydrocarbyl or hydrocarbylcarbonyl group;
$R^8$ represents a substituted or unsubstituted hydrocarbyl group; and
$R^P$ a) has the same meaning as $X^P$, whereby the compound of formula (III) may be symmetrical or unsymmetrical; or
b) is a group of the following formula (V):

(V)

wherein
$Y^P$ represents a single bond, an oxygen atom or a group NR', wherein R' represents a substituted or unsubstituted hydrocarbyl group;
$R^9$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
c) when M is Si, $R^P$ may be a substituted or unsubstituted hydrocarbyl group.

It was surprisingly found that photoinitiator compounds of formula (III) represent polymerization initiators which are particularly suitable for dental compositions. With compounds of formula (III), a high polymerization efficiency is attained, and no coloration problems occur, or in a polymerization system comprising a conventional photoinitiator such as camphor quinone, coloration is efficiently suppressed. Furthermore, compounds of formula (III) have a light absorption within the wavelength range typically applied in dental application, they are compatible with the ingredients of dental compositions and besides, they are considered physiologically harmless.

Therefore, compounds of formula (III) are particularly preferred as photoinitiators.

In connection with compound of formula (III), the term "substituted" as used herein means that $R^6$, $R^7$, $R^8$, $R^9$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^6$, $R^7$ and $R^8$ are substituted, then it is preferred that they are substituted with 1 to 3 substituents, more preferably with 1 substituent.

In the compound of formula (III), moieties $R^6$, $R^7$ and $R^8$ may be defined as follows:

$R^6$ and $R^7$ independently from each other represent a substituted or unsubstituted hydrocarbyl or hydrocarbylcarbonyl group, and $R^8$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl (-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl (-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and napthyl.

The hydrocarbylcarbonyl groups of $R^6$ and $R^7$ represent acyl groups ($R_{org}$—(C=O)—) in which the organic residue $R_{org}$ is a hydrocarbyl residue as defined above.

Compound of formula (III) may contain one or two hydrocarbylcarbonyl groups, that is either one of $R^6$ or $R^7$ is a hydrocarbylcarbonyl group, or both $R^6$ and $R^7$ are hydrocarbylcarbonyl groups. Preferably, compound of formula (III) contains one hydrocarbylcarbonyl group.

Preferably, the hydrocarbylcarbonyl group is an arylcarbonyl group, more preferably a benzoyl group.

Preferably, $R^6$ and $R^7$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-6}$ alkyl group or a phenyl group.

Most preferably, $R^6$ and $R^7$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-4}$ alkyl group.

In the compound of formula (III), $R^P$ may have the same meaning as X, whereby the compound of formula (III) may be symmetrical or unsymmetrical. Alternatively, $R^P$ may represent a substituted or unsubstituted hydrocarbyl group, or a group of formula (V). Preferably, if $R^P$ has the same meaning as X, then compound of formula (III) is unsymmetrical. If $R^P$ represents a substituted or unsubstituted hydrocarbyl group, then the hydrocarbyl group has the same meaning as defined above for $R^6$ and is independently selected therefrom.

In the group of formula (V) of compound of formula (III), $R^9$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilylgroup.

If $R^9$ of formula (V) is a trihydrocarbylsilyl group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^6$, $R^7$ and $R^8$ and is independently selected therefrom.

In formula (V), R' has the same meaning as defined for $R^8$ and is independently selected therefrom.

If M is Si in compound of formula (III), $R^P$ may be also be a substituted or unsubstituted hydrocarbyl group, wherein the hydrocarbyl group has the same meaning as defined above for $R^8$ and is independently selected therefrom.

For example, compounds of formula (III) wherein $R^P$ has the same meaning as $X^P$ and which are symmetrical may be have the following structural formulae:

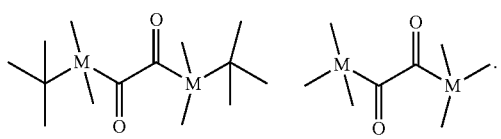

For example, compounds of formula (III) wherein $R^P$ represents a group of formula (V) wherein $Y^P$ is a bond, an oxygen atom or a NR' group, and $R^9$ represents a substituted or unsubstituted hydrocarbyl group may have the following structural formulae:

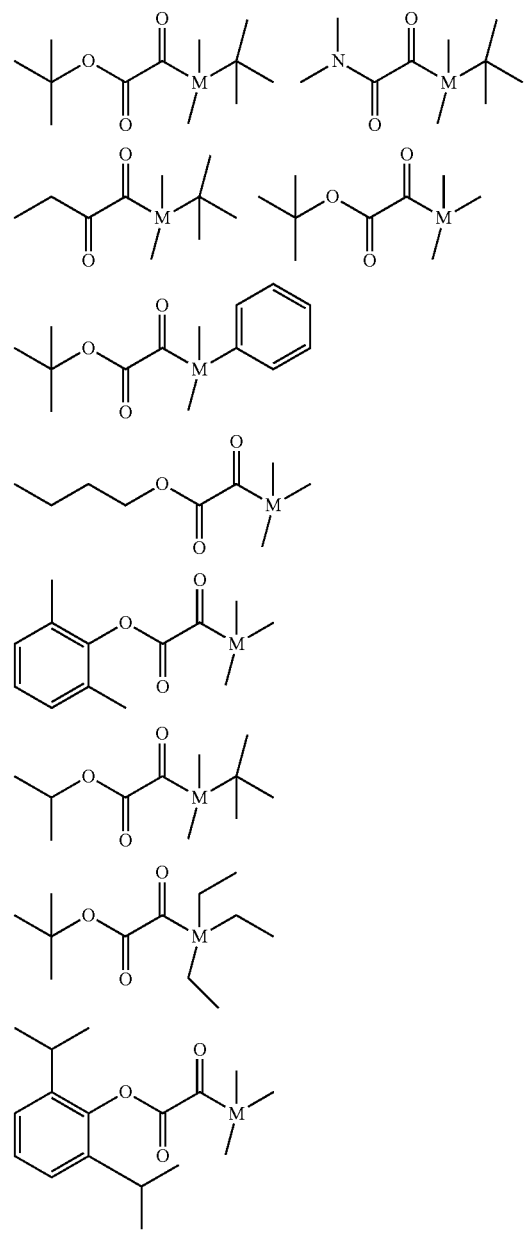

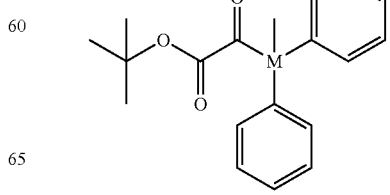

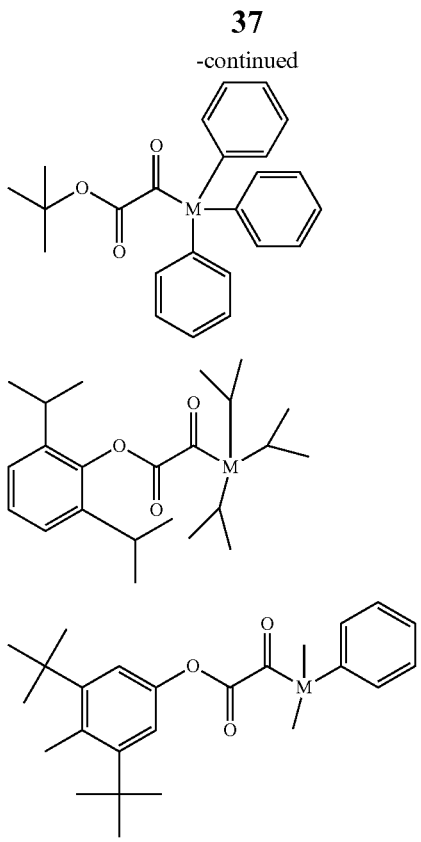
For example, compounds of formula (III) wherein $R^P$ represents a group of formula (V) wherein $R^9$ represents a trihydrocarbylsilyl group have the following structural formulae:
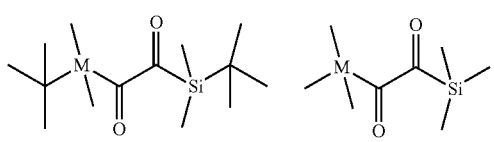
For example, compounds of formula (III) wherein M is Si and $R^P$ represents a substituted or unsubstituted hydrocarbyl group, may have the following structural formulae:
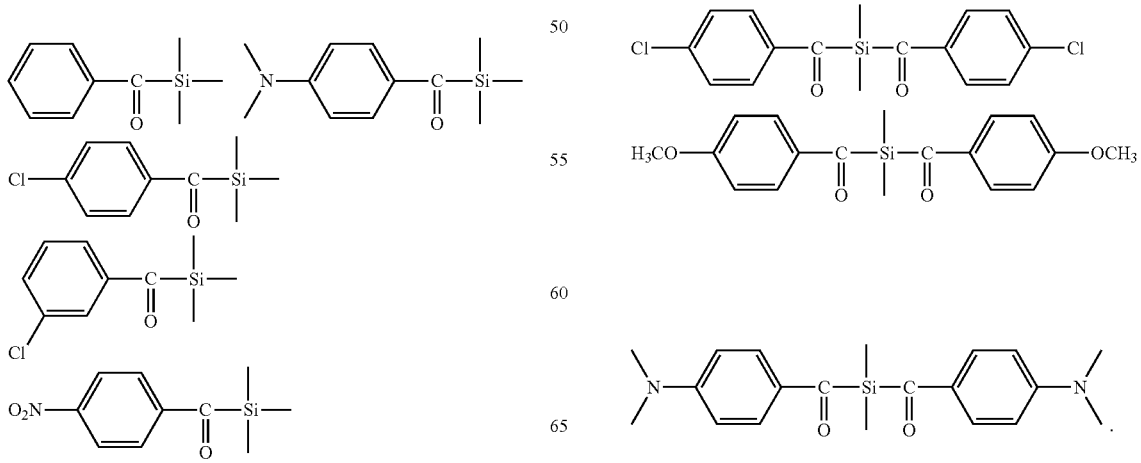

Preferably, compound of formula (III) is selected from the group consisting of:

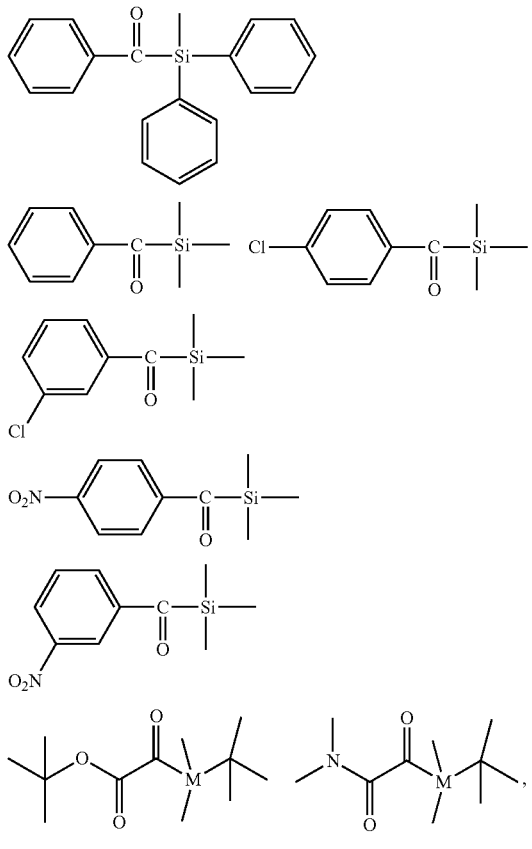

wherein compounds of formula (III) with M=Si are particularly preferred.

Most preferably, compound of formula (III) is selected from the group consisting of: compound of formula (III) is selected from the group consisting of:

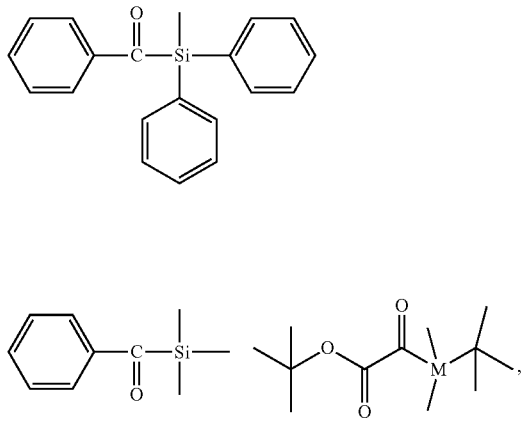

wherein it is particularly preferred that M=Si.

In case the dental composition is in the form of an acidic composition, that is a composition having a pH of less than 7, depending on the composition's pH level, it is preferred to select compounds of formula (III) with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are compounds of formula (III) excluding $R^P$ being a group of formula (V) in which $Y^P$ is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (III) may be a known compound which is commercially available or a may be prepared according to published procedures.

The compound of formula (III) wherein M is Si and $R^P$ represents a substituted or unsubstituted hydrocarbyl group may for example be readily prepared by means of a one-step Pd-catalyzed reaction with a disilane as described e.g. by Yamamoto K. et al., *J. Tetrahedron Lett.*, 1980, vol. 21, pages 1653 to 1656:

Scheme 1 Preparation of acylsilanes

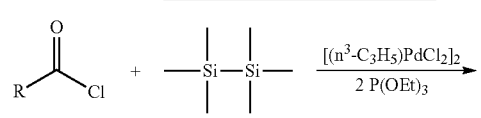

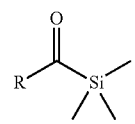

In Scheme 1, the reaction is exemplary depicted with hexamethylsilan as the disilane, whereby a compound of formula (III) wherein $R^6$, $R^7$ and $R^8$ represent a methyl group is obtained. It is understood that $R^6$, $R^7$ and $R^8$ can be varied by applying disilanes having hydrocarbon substituents other than methyl.

The compound of formula (III) wherein $R^P$ represents a group of formula (V) in which $Y^P$ is an oxygen atom and $R^9$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyl-trifluoromethane-sulfonate to obtain a trihydrocarbylsilyldi-azoacetate, which is finally reacted with potassium peroxymonosulfate to arrive at the target compound:

Scheme 2 Preparation of silylglyoxylates

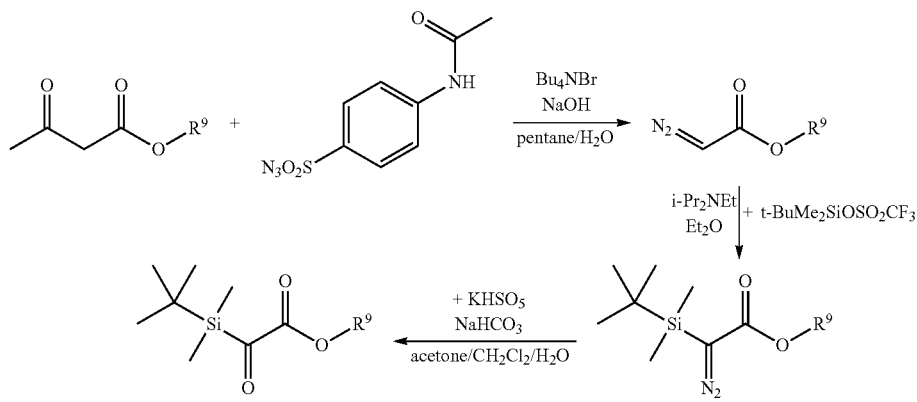

In Scheme 2, the reaction is exemplary depicted for obtaining a compound of formula (III) wherein $R^9$ of group (V) represents a hydrocarbyl group in the form of tert-butyl. It is understood that $R^9$ can be varied by applying an acetoacetate other than tert-butyl acetoacetate.

Alternatively, compounds of formula (III) wherein M is Si, $R^P$ represents a group of formula (V) and $Y^P$ represents an oxygen atom may be prepared by a single-pot three-component coupling reaction of a silylglyoxylate, a terminal alkyne and an aldehyde in the presence of $ZnI_2$ and $Et_3N$ as described by Nicewicz D. A. in J. Am. Chem. Soc., 2005, 127 (17), pages 6170 to 6171. Further syntheses of silylglyoxylate compounds are described e.g. by Boyce G. R. et al. in J. Org. Chem., 2012, 77 (10), pages 4503 to 4515 and Boyce G. R. et al. in Org. Lett., 2012, 14 (2), pages 652 to 655.

For example, the following compounds of formula (III) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

All compounds of formula (III) comprise the group of formula (IV),

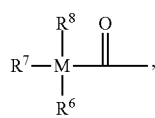
(IV)

wherein M, $R^6$, $R^7$ and $R^8$ are defined as above. Depending on the selection of M, the group of formula (IV) represents an acylsilane or acylgermane group. Upon exposure to UV-VIS-light, the bond between M and the acyl group may be cleaved, whereby a silyl/germanyl and an acyl radical is formed as a polymerization initiating structure, but in competition to the cleavage into to radicals, a carbene structure might be formed:

Scheme 3 carbene formation versus radical formation

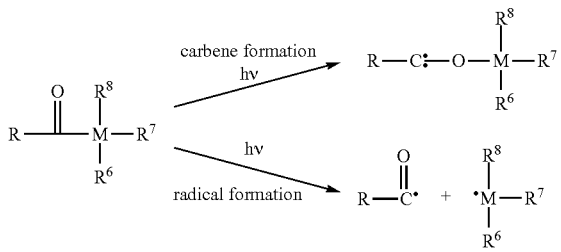

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (III) wherein $R^P$ has the same meaning as $X^P$ or is a group of formula (V), the C—C bond of the 1,2-diketone moiety (—C(=O)—C(=O)—) may be cleaved upon exposure to UV-VIS-light into two acyl radicals. This cleavage is exemplary shown for compound of formula (III) wherein $R^P$ is a group of formula (V) and $Y^P$ is an oxygen atom, that is for a glyoxylate (—O—C(=O)—C(=O)—) compound:

Scheme 4 cleavage of
—O—C(=O)—C(=O)— moiety
of a glyoxylate

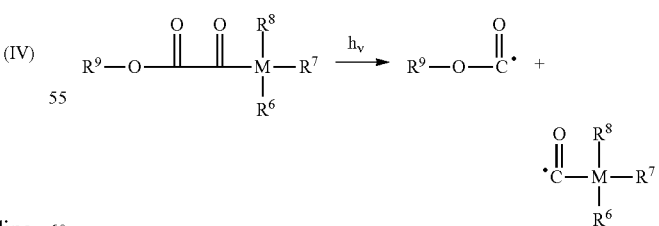

Besides, in compound of formula (III), there is a third possibility for a radical cleavage in case $R^P$ is a compound of formula (V) wherein $Y^P$ is an oxygen atom and $R^9$ is a substituted or unsubstituted hydrocarbyl group. Namely, an intra- or intermolecular hydrogen abstraction might occur, where a hydrogen radical is abstracted:

Scheme 5 hydrogen abstraction (intra- or intermolecular)

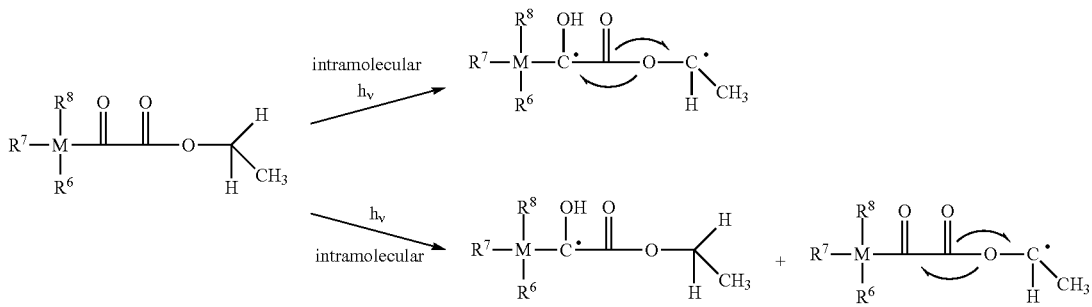

Both the cleavage of a glyoxylate group and the hydrogen abstraction mechanism is known for photoinitiators which do not contain silicium or germanium, such as ethyl phenylglyoxylate (Irgacure® MBF).

For compounds of formula (III) wherein $R^P$ has the same meaning as $X^P$ or is a group of formula (V), the present inventors carried out molecular modelling calculations from which it appears that a Si—C or Ge—C bond cleavage can be ruled out, since the C—C bond of the —C(=O)—C (=O)— moiety is weaker than the Si—C or Ge—C bond.

The photoinitiator system may further comprise diaryl iodonium salts, triaryl sulfonium salts and tetraaryl or tetraalkyl phosphonium salts. These salts may serve as a coinitiator for improving the polymerization performance of the photoinitiator, but they may also serve as an initiator for cationic polymerization.

For example, diaryl iodonium salt may be selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl]iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

A preferred friaryl sulfonium salt is S-(phenyl)thianthrenium hexafluorophosphate of the following formula:

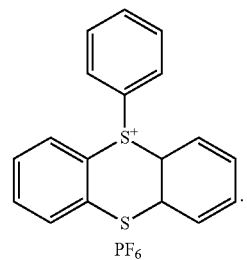

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

A particularly preferred photoinitiator system comprises a photoinitiators of formula (III), optionally in addition with camphor quinone, in combination with a diaryl iodonium salt, triaryl sulfonium salt or a tetraaryl or tetraalkyl phosphonium salt as described above.

A suitable redox initiator system comprises reducing and oxidizing agents, which produce free-radicals capable of initiating polymerization of the polymerizable group(s) of polymerizable compound(s) (ii) or further polymerizable compounds independent from the presence of light. The reducing and oxidizing agents are selected so that the initiator system (iii) is sufficiently storage-stable and free of undesirable colorization to permit storage and use under typical dental conditions. Moreover, the reducing and oxidizing agents are selected so that the initiator system (iii) is sufficiently miscible with the resin system to permit dissolution of the initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

The amount of active species of the initiator system (iii) is not particularly limited. Suitably, the amount of photoinitiator in the initiator system (iii) is in the range of from 0.001 to 5 mol % based on the total amount of the one or more polymerizable compounds (ii) or further polymerizable compounds described below.

Further Optional Components

The dental composition according to the present invention may, besides of the above described optional components, comprise additional optional components.

For example, the dental composition according to the present invention may comprise suitable solvents. These solvents may be selected from water, alcohols such as methanol, ethanol, propanol (n-, i-), butanol (n-, iso-, tert.-), and ketones such as acetone or the like.

The dental composition of the present invention may comprise the solvent in an amount of 5 to 75 percent by weight based on the total weight of the composition.

Besides of the structural filler (A) and the silanated glass flakes (B), the dental composition may comprise a further filler (C), which is preferably at least one selected from the group consisting of granulated prepolymerized fillers, a ground prepolymerized fillers and filler aggregates.

The aforementioned filler aggregates may be obtained by a process comprising:

(a) coating a particulate filler having a median particle size (D50) of from 1 to 1200 nm with a coating composition containing a polymerizable film-forming agent forming a polymer coating layer on the surface of the particulate filler, said polymer coating layer may display reactive groups on the surface of the coating layer, said reactive groups being selected from addition polymerizable groups and step-growth polymerizable groups, thereby forming a coated particulate filler; subsequently or concurrently (b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(c) optionally milling, classifying and/or sieving the granulation of the coated particulate filler; and (d) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP 2 604 247 A1.

For obtaining granulated and ground prepolymerized fillers, step (b) of the above described process is omitted, and the milling step (c) is applied with a suitable milling apparatus to attain an appropriate granulation particle size or ground particle size.

Preferably, the further filler (C) is silanated, more preferably silanated with an organosilane as described above for the silanated glass flakes (B).

The dental composition of the present invention may further contain preservatives, pigments, free radical scavengers, reactive and nonreactive diluents, coupling agents to enhance reactivity of fillers, rheology modifiers, and surfactants.

Suitable preservatives may be selected from reducing agents such as vitamin C, inorganic sulfides and polysulfides and the like.

Preferably, the dental composition according to the invention does not comprise a polymerizable polymer containing at least two (meth)acrylate groups. Most preferably the dental composition according to the invention does not comprise a polymerizable polymer.

The invention will now be further illustrated by the following Examples.

EXAMPLES

1. Gloss and Gloss Retention Testing

The dental composition according to the invention is placed in transparent molds having suitable dimensions (e.g. 20 mm×10 mm×5 mm) and cured with a suitable dental curing light such as SmartLite® Focus (from Dentsply DeTrey GmbH, Germany) with a predetermined wavelength and power for a predetermined time. The resulting samples may be used as obtained from the molds, or they may be polished by a predefined polishing treatment typically used in the field of dental restoration for e.g. adapting the location of the tooth treated with the dental composition to the original surface shape of the tooth.

Then, the initial gloss of the surface of the above described polished or unpolished samples is determined. The initial gloss can be measured by a suitable glossmeter, such as Novo Curve Small Area Glossmeter (from the company Rhopoint Instruments Ltd., Great Britain).

Gloss Retention in View of Wear Resistance

The gloss retention behavior of the above described polished or unpolished samples is tested in view of wear resistance by applying a tooth brushing machine, preferably one in accordance with ISO/TS 14569-1. The tooth brushing machine presses its brush against a sample with an suitably selected load (e.g. 1.4 N), and the brush carries out a reciprocating movement typical for tooth brushing. Further, when applying the tooth brushing machine, the temperature of the toothpaste slurry is preferably kept at a typical and constant temperature, for example room temperature, e.g. at 20±3° C. The abrasive slurry is prepared from a mixture of a conventional toothpaste and deionized water in an appropriate ratio, for example 2 g of water to 1 g of toothpaste.

The total brushing time with the brushing machine is suitably selected, for example 720 minutes. For a predetermined period of time, e.g. every sixty minutes of the application of the tooth brushing machine, gloss is measured using a glossmeter. The gloss retention in view of wear resistance may for example be recorded until the surface gloss of the sample is low, that is decreased to a value of less than 10 G.U. at a measuring angle of 60°.

2. Gloss Retention in View of Chemical Resistance

Gloss retention in view of chemical resistance is tested by placing the above described polished or unpolished samples into a fluid having a pH within the range of about 6.5 to 6.9 and an appropriate mineral composition for simulating saliva, or into a fluid having a pH lower than saliva to reflect the daily load of acidity by means of food. For a predetermined period of time, e.g. every seven days (168 h), gloss is measured using a glossmeter. The gloss retention in view of chemical resistance may for example be recorded until the surface gloss of the sample is low, that is decreased to a value of less than 10 G.U. at a measuring angle of 60° .2. Adhesion to the enamel of teeth Extracted teeth such as human or bovine molars are provided and may be immersed in water at a predetermined temperature for a predetermined time prior to use, for example 4° C. for 24 hrs. The enamel of the teeth is appropriately prepared, for example by sanding, e.g. by using wet 320 grit abrasive paper and then 600 grit abrasive paper under running water.

Then, the dental composition according to the invention is applied to the extracted teeth, for example by using a gelatin capsule post. The gelatin capsule post (e.g. having 4.5 mm in diameter), which is open at one end, is filled with a dental composition according to the invention. A sanded area of the tooth is positioned at the open end of the filled gelatin capsule post such that the sanded area fully contacts the dental composition at the open end of the gelatin capsule post. Excess dental composition is removed from the surface of the capsule posts using a dental explorer. Then, the filled posts are light-cured with a suitable dental curing light such as SmartLite® Focus dental curing light (from Dentsply DeTrey GmbH, Germany) with a predetermined wavelength and power for a predetermined time for three times around the post to adhere the posts to the polished surface. The substrate samples with bonded gelatin posts are placed in a distilled water bath for a predetermined temperature and time before testing for shear bond strength, e.g. 37° C. for 24 hours.

Then shear bond strength testing is carried out by using an appropriate apparatus, e.g. an Instron Model 4400 electromechanical testing unit (from the company Instron, USA) with a crosshead speed of 1 mm/min.

3. Viscosity and Thixotropy

The workability of the present dental composition in view of its flow properties may be suitably set by varying the size of structural filler (A) and silanated glass flakes (B), and by varying the amount of structural filler (A) and silanated glass flakes (B). The dental compositions according to the invention having differently sized and/or different amounts of structural filler (A) and silanated glass flakes (B) are then measured with a suitable rotational rheometer and compared with each other.

4. Preparation of Silanated Glass Flakes (B) by Milling and Coating

Method for measuring the average particle size ($d_{3,50}$) of the glass flakes: A small amount of glass flakes was directly added into the measuring cell of a Malvern Mastersizer 3000, containing 800 mL of water and being equipped with a stirrer set to 2200 U/min and an ultrasound probe set to 80%. The actual amount of flakes added here was depending on the laser shadowing detected by the measuring device. The amount of added flakes lead to laser shadowing of 8-15%. The average particle size was measured after applying ultrasound from the ultrasound probe in the measurement cell under stirring for 2 minutes. Ultrasound was applied to break up loosely aggregated/layered flakes.

Example 1

Milling of Flakes by Means of Pearl Mill

The grinding container of the mill (Dyno-mill Multi Lab, Willy A. Bachofen AG Maschinenfabrik) was filled with 450 mL grinding beads (soda-lime glass, 0.75-1 mm). In a storage tank 50 g ECR glassflakes GF350 nmM (from Glass Flake Ltd., Leeds, England) without surface functionalization were dispersed in 1.5 L water. A homogeneous dispersion was maintained by continuous stirring. The dispersion was pumped by a peristaltic pump into the grinding container and returned from the mill outlet into the storage tank. After 15, 30, 45 and 60 min samples were collected at the mill outlet. The average particle size d3,50 of the milled flakes are listed in Table 1 below:

TABLE 1

Grinding time in pearl mill and resulting average particle size ($d_{3,50}$)

| Experiment: | Grinding time [min] | Average particle size $d_{3,50}$ [μm] |
|---|---|---|
| Run 1 | 15 | 27.0 |
| Run 2 | 30 | 17.6 |
| Run 3 | 45 | 13.4 |
| Run 4 | 60 | 11.3 |

For further experiments, 100 g of ECR glassflakes GF350 nmM without surface functionalization were dispersed in each case in 2.0 L of water and processed via pearl mill. The average particle size obtained for each run is stated in the following table:

TABLE 2

Four grinding batches and their resulting average particle size ($d_{3,50}$)

| Experiment: | Grinding time [h] | Average particle size $d_{3,50}$ [μm] |
| --- | --- | --- |
| Run 1 | 0.5 | 26.9 |
| Run 2 | 1 | 17.1 |
| Run 3 | 2 | 11.4 |
| Run 4 | 4 | 3.5 |

For further processing, the flakes were separated from water by sedimentation. The supernatant was discarded. The sedimented flakes were dried at 80° C. for about 16 h and sieved through a 180 μm sieve for deaggregation.

Example 2

Coating of Flakes

Flakes of Example 2, Run 1 to 4, were dispersed in about five times the amount of 2-propanol and stirred for 1 h. During stirring, the suspension was treated with ultrasound. 3 wt-% of 3-(trimethoxysilyl)propyl methacrylate (related to the flake amount) were added drop-wise to the suspension. Subsequently, the solvent was removed in vacuo, and the residue was dried at 80° C. for about 16 h. The coated flakes were sieved through a 180 μm sieve for deaggregation.

In a beaker containing about 50 mL water, a portion of about 50 mg of the coated flakes was placed on the surface, whereby the coated flakes stay afloat, which indicates that the flakes have been coated with hydrophobic 3-(trimethoxysilyl)propyl methacrylate.

Without any washing of the flakes prior to coating, when adding the unwashed flakes into a dental composition as described in Example 4, greyish pastes were obtained. For better aesthetical results, the flakes may be washed prior to coating. For washing, the flakes may be stirred in twice the amount of 2.5% hydrochloric acid for half an hour, and then filtered off and washed with about the twentyfold amount of water during filtration. Finally, the flakes may be dried at 80° C. for about 16 h.

5. Dental Composition in the Form of a Paste Comprising Dental Filler (i)

Example 3

Paste Preparation

Pastes were produced by placing the coated flakes of Example 2, a further filler in the form of the commercially available composite Ceram.x® universal ($YbF_3$, silanized 0.6 μm Ba glass), and a monomer mixture of the commercially available composite Ceram.x® universal—comprising dimethacrylate resins, methacrylate modified polysiloxane, fluorescent pigment, UV stabilizer, stabilizer, initiator system—in a plastic container. The $YbF_3$ content of each paste was 4 wt-%. The total filler content of each paste was 74 wt-%. The plastic container was placed in a Speed-Mixer (Hausschild Engineering) and the components therein homogenized. The thus obtained pastes were analyzed. The analysis results are summarized in the following table:

TABLE 1 characteristics of pastes

| Paste No: | grinding time of glass flakes [h] | percentage of coated flakes based on coated flakes and Ba glass [%] | Extrusion force[1] [N] | Flexural strength[2] [MPa] | E-modulus [GPa] |
| --- | --- | --- | --- | --- | --- |
| 1 | —[3] | 0 | 198 | 135 | 8.5 |
| 2 | 0.5 | 0.15 | 63 | 133 | 10.3 |
| 3 | 0.5 | 0.35 | 46[4] | 160[4] | 11.9[4] |
| 4 | 0.5 | 0.55 | 94 | 117 | 13.1 |
| 5 | 1 | 0.15 | 60 | 154 | 9.8 |
| 6 | 1 | 0.418 | 63 | 167 | 12.6 |
| 7 | 1 | 0.55 | 109 | 128 | 12.4 |
| 8 | 2 | 0.15 | 76 | 145 | 9.9 |
| 9 | 2 | 0.35 | 50[4] | 174[4] | 11.7[4] |
| 10 | 2 | 0.55 | 93 | 135 | 11.2 |
| 11 | 4 | 0.15 | 193 | 142 | 9.1 |
| 12 | 4 | 0.35 | 274[4] | 155[4] | 9.4[4] |
| 13 | 4 | 0.55 | 324 | 114 | 9.9 |

[1] extrusion force from Dentsply compule (nozzle diameter 1.8 mm) used for ceram.x universal
[2] determined according to ISO 4049: 2009
[3] paste containing solely Ba glass
[4] average value derived from two different pastes (same formulation, same raw materials)
In Table 3, the term "grinding time of glass flakes" refers to the grinding time applied to the uncoated glass flakes in Example 1 prior to the coating of the glass flakes in Example 2.

From Table 3 it can be seen that pastes no. 2, 3, 5, 6, 9 according to the invention show an advantageous low extrusion force for extruding the uncured dental composition through a nozzle. By contrast, when the silanated glass flakes (B) are absent like in paste no. 1, then the extrusion force becomes unfavorable high. Furthermore, from pastes no. 11 to 13 it can be seen that a relatively long grinding time of the flakes of 4 hours, which results in a small average particle size $d_{3,50}$ of the glass flakes of about 3.5 μm, may lead to an undesired increase of the extrusion force.

Example 4

SEM Pictures

Scanning electron microscopy (SEM) pictures were taken using an ultra-high resolution FESEM from Zeiss.

FIG. 1 to FIG. 4 show the flakes listed in Table 2 after silanization according to example 2. Specifically, FIG. 1 shows ECR Glassflakes GF350 nmM after grinding for 0.5 h and silanization. FIG. 2 shows ECR Glassflakes GF350 nmM after grinding for 1 h and silanization. FIG. 3 shows ECR Glassflakes GF350 nmM after grinding for 2 h and silanization. FIG. 4 shows ECR Glassflakes GF350 nmM after grinding for 4 h and silanization.

COMPARATIVE EXAMPLE 1

US 20060241205 'Filler Materials For Dental Composites'

In example E and G to I of US 20060241205, pastes are disclosed containing a polymerizable resin mixture and silane-treated glass flakes in combination with a further filler. The silane-treated glass flakes have a thickness of 5 μm and either an average glass flake dimension of about 15 microns or of about 160 microns. In case of examples E and H the ratio of flakes to silane-treated glass filler is 40 to 60.

Following those examples, pastes containing silanized flakes of 350 nm and 5 μm, respectively, and 0.6 μm Ba glass were prepared. The total filler content of 74.0% and a flake to 0.6 μm Ba glass ratio of 40 to 60 was used. The flakes used for paste preparation are listed in the following table 4:

TABLE 4 experimental pastes containing flakes of various nominal thickness

Figure 1:
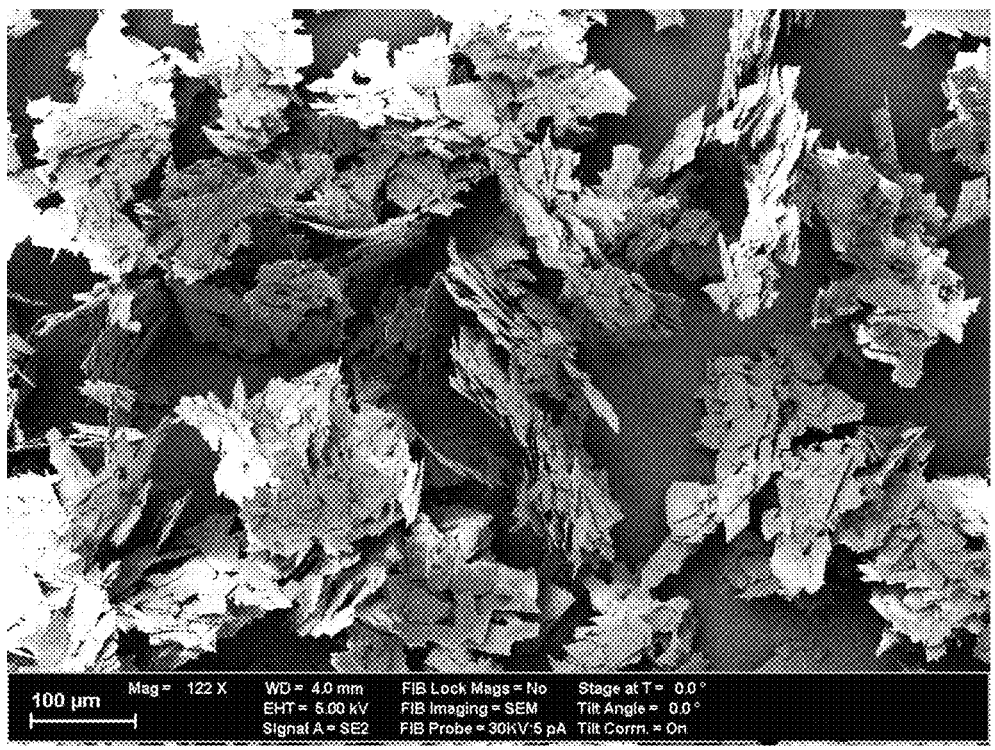
Figure 2:
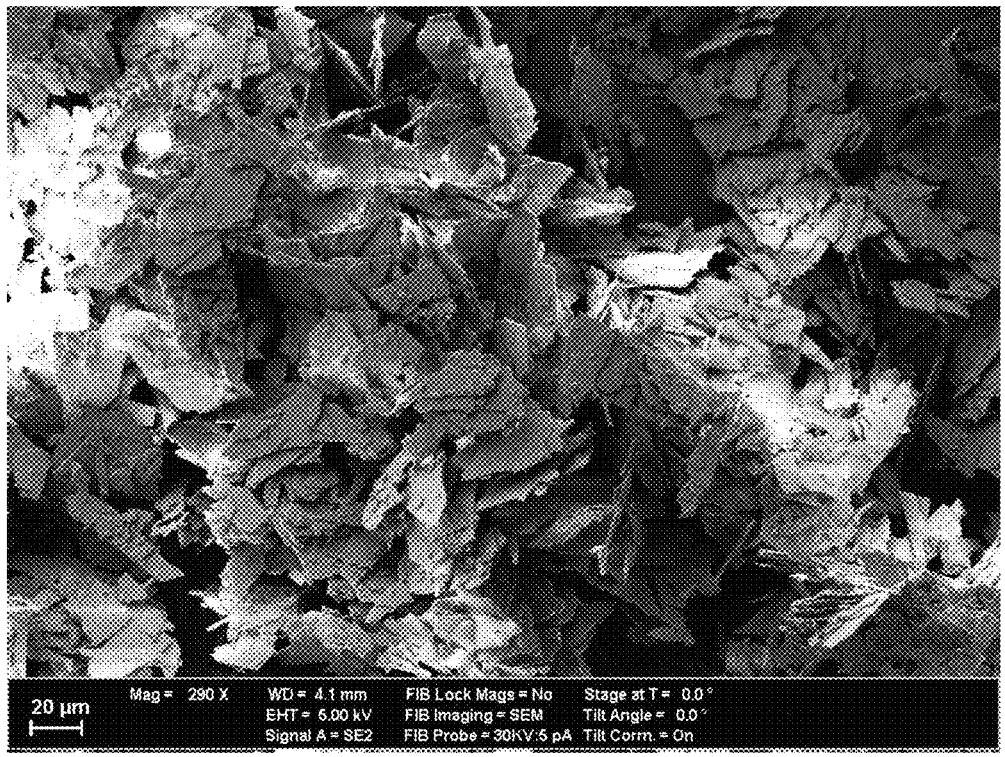
Figure 3:
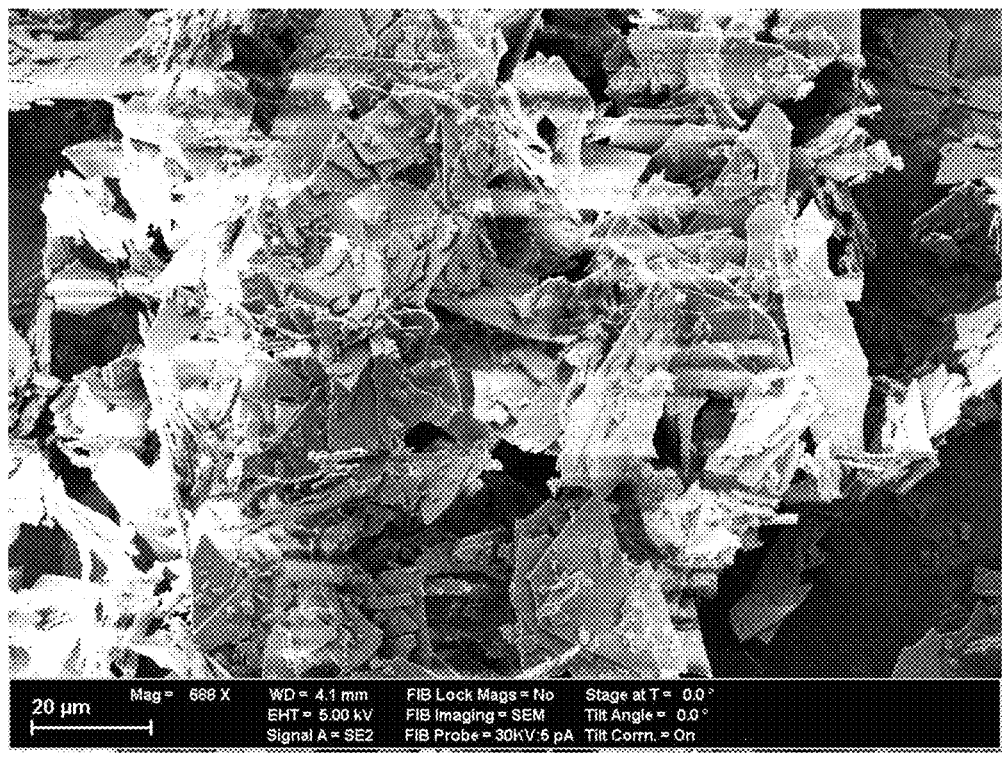
Figure 4:
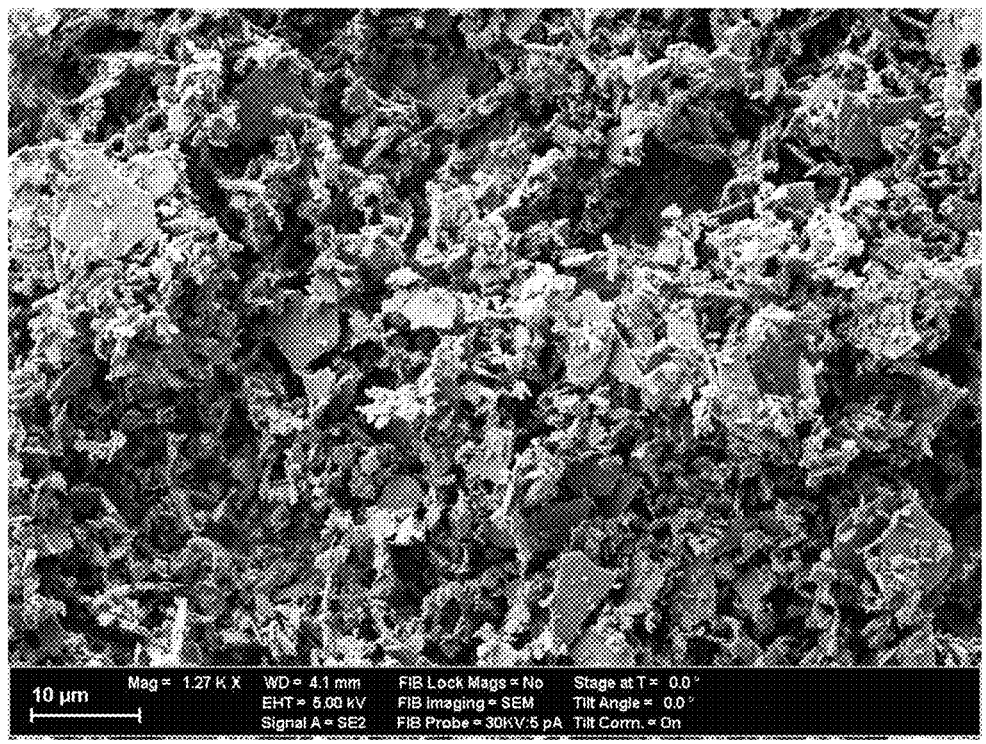
Figure 5:
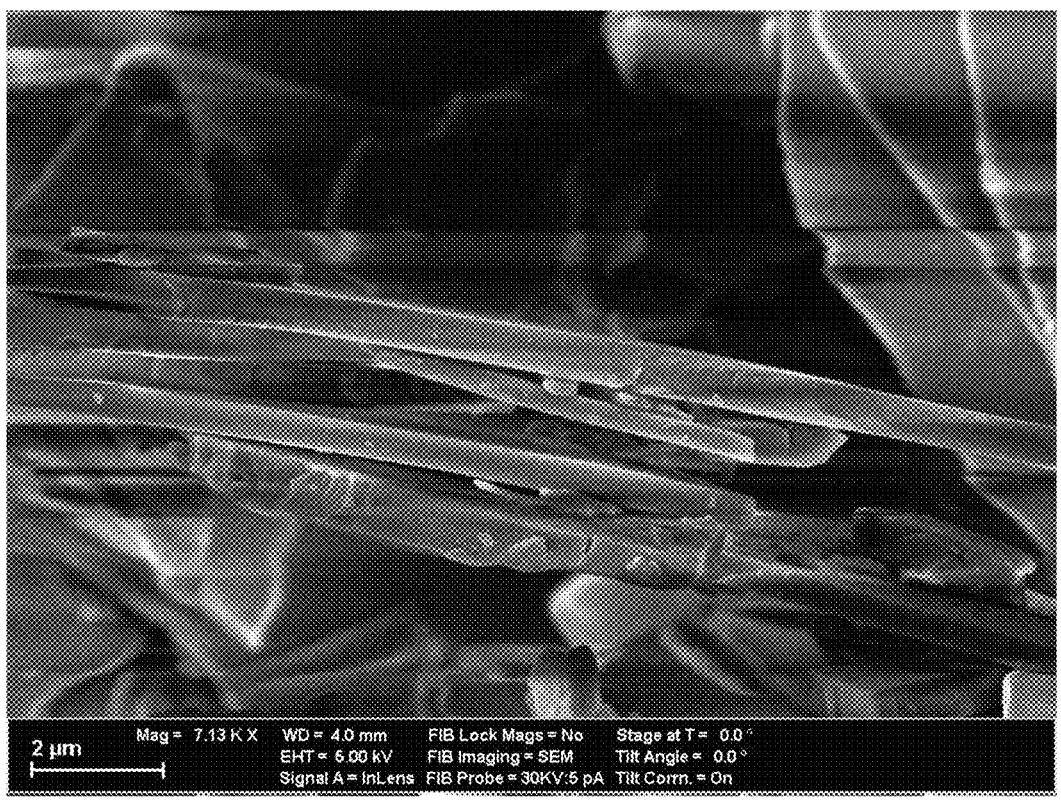
FIG. 5 and FIG. 6 show ECR glass flakes with a nominal thicknesses of 350 nm and 5 μm, respectively.
Figure 6:
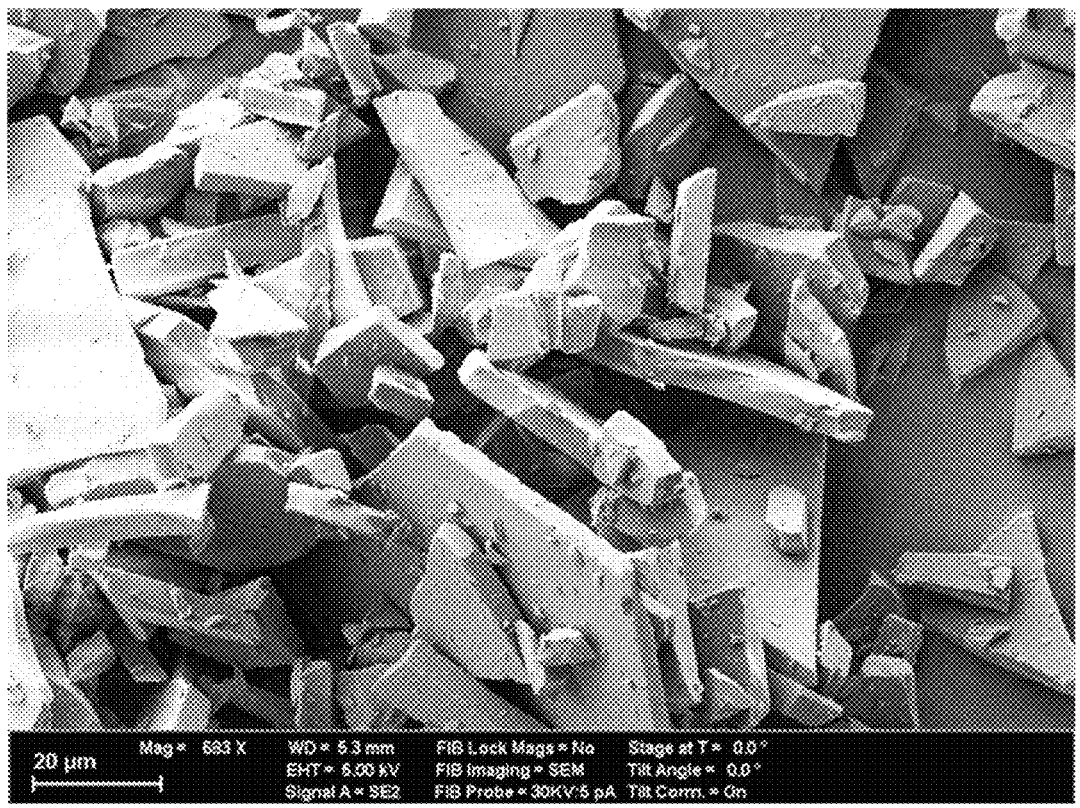
Figure 7:
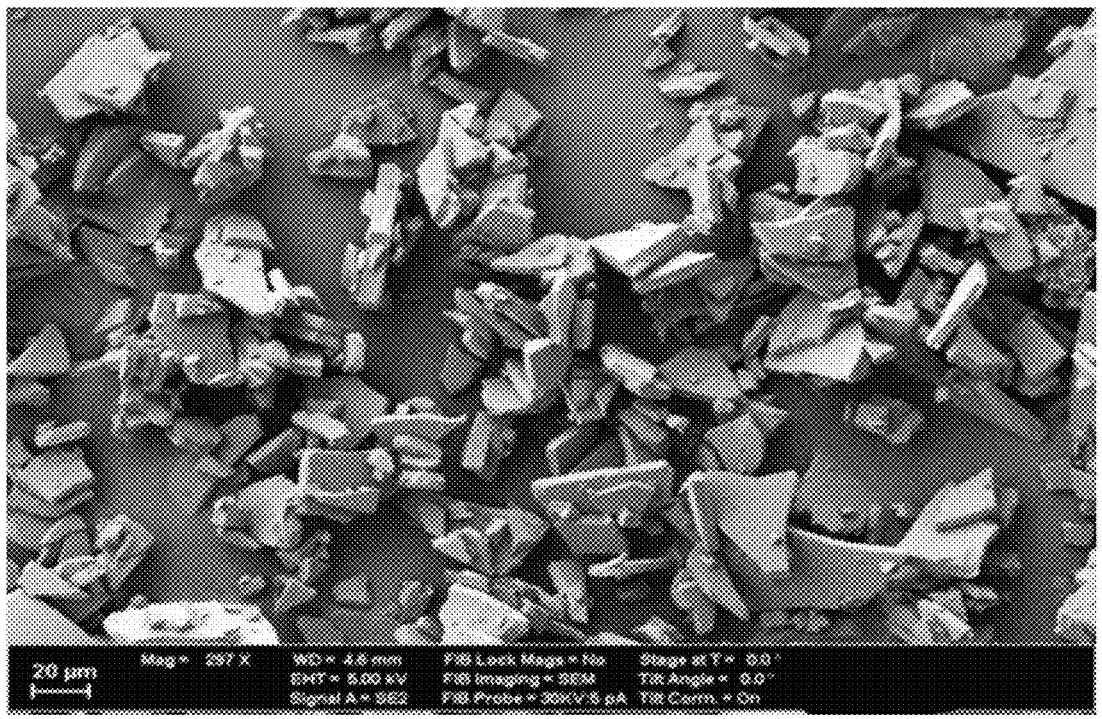
FIG. 7 and FIG. 8 show ECR glass flakes with a nominal thickness of respectively.
Figure 8:
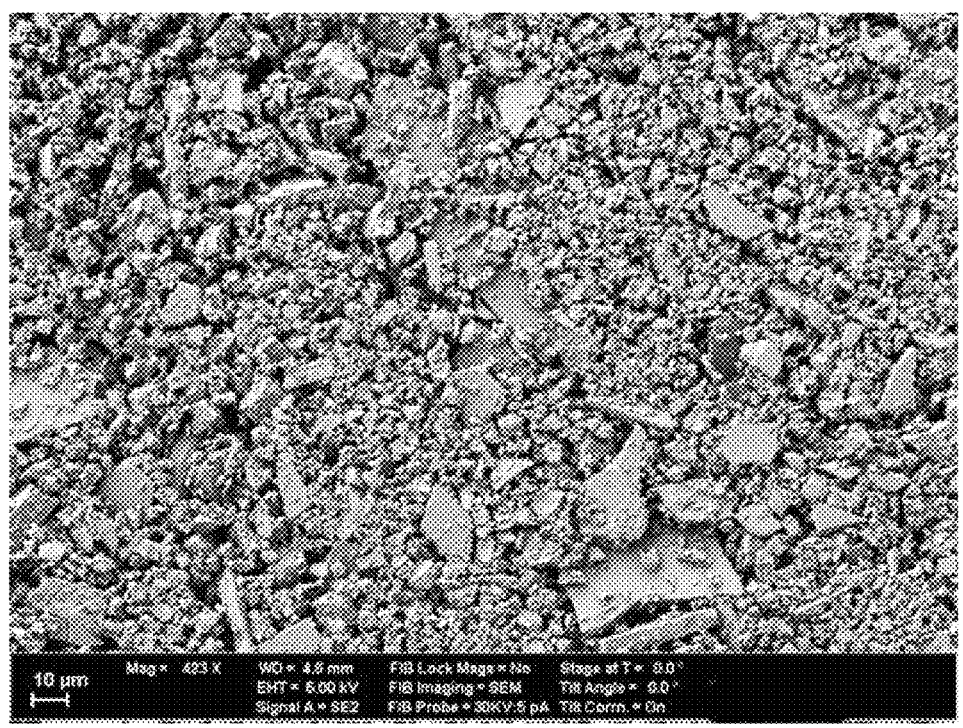
Figure 9:
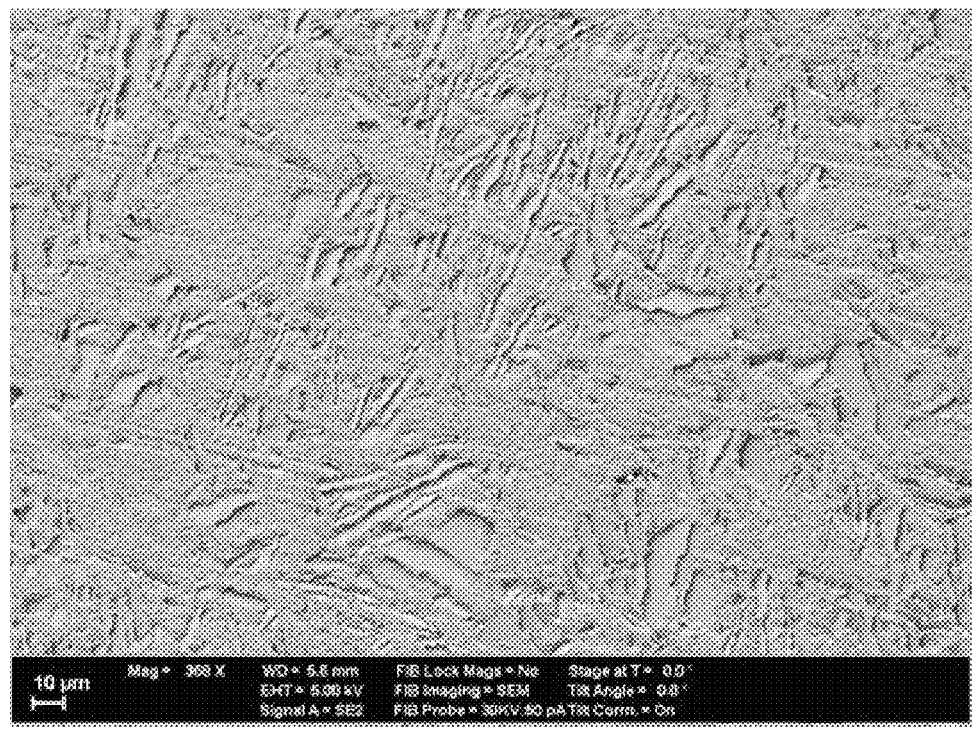
FIG. 9 shows a composite containing glass flakes.

| Paste No. | Untreated Glass Flakes | | | Median flake size $d_{3,50}$ | FIG. no.[3] |
|---|---|---|---|---|---|
| | Name | Nominal Thickness[1] | Grinding time | | |
| 1 | ECR GF350 nmM | ca. 350 nm | 1 h | 17.1 μm | FIG. 2 |
| 2 | ECR GF350 nmM | ca. 350 nm | 2 h | 11.4 μm | FIG. 3 |
| 3 | ECR GF007 | 4-6 μm | no grinding | 30.8 μm | FIG. 7 |
| 4 | ECR GF007 | 4-6 μm | 2 passages[2] | 12.0 μm | FIG. 8 |

[1] Nominal flake thickness acc. to manufactures technical data sheet
[2] Instead of circulating the suspension via the pearl mill, the flake suspension was pumped once via the pearl mill and collected at the mill outlet in a separated bucket (=1 passage). When necessary this procedure was repeated.
[3] SEM pictures were taken after silanization according to example 2

After grinding the flakes were silanized according to Example 2 and the pastes prepared according to example 3. The results of the flexural strength and E-modulus determinations of the four pastes are summarized in Table 5:

TABLE 5 experimental pastes containing flakes of various nominal thickness

| Paste No. | Flexural strength[1] MPa | E-modulus GPa |
|---|---|---|
| 1 | 161 | 12.1 |
| 2 | 163 | 11.7 |
| 3 | 144 | 10.2 |
| 4 | 141 | 9.3 |

[1] determined according to ISO 4049: 2009

From Table 5 it can be seen that for an identical formulation the flexural strength and E-modulus is favorably higher in case of the thinner flakes (nominal thickness of 350 nm, paste no. 1 and 2) compared to the thicker flakes (nominal thickness of 5 μm, paste no. 3 and 4).

The invention claimed is:

1. A dental composition comprising:
   (i) a dental filler containing
      (A) a structural filler having an average particle size of from 0.1 to 3 μm; and
      (B) silanated glass flakes,
         (a) wherein the silanated glass flakes have an average thickness between 50 nm and 1000 nm; and
         (b) wherein the silanated glass flakes have an average aspect ratio (long diameter/thickness) in the range of from 2:1 to 50:1;
   (ii) one or more polymerizable compounds; and
   (iii) an initiator system.

2. The dental composition according to claim 1, wherein the glass of the silanated glass flakes (B) comprises the following components as oxides in percent by weight:
   $SiO_2$=64-70
   $B_2O_3$=2-5
   ZnO=1-5
   $Na_2O$=8-13
   MgO=1-4
   CaO=3-7
   $Al_2O_3$=3-6
   and up to 3 percent of $K_2O$ and $TiO_2$, and/or
   wherein the structural filler (A) is a dental glass selected from the group consisting of
      inert glasses, reactive glasses and fluoride releasing glasses.

3. The dental composition according to claim 1, wherein the silanated glass flakes (B) include silanated glass flakes having a thickness of 30 nm to 1500 nm in an amount of at least 90% by weight.

4. The dental composition according to claim 1, wherein the silanated glass flakes (B) are obtained by milling glass flakes having an aspect ratio of at least 20:1, and subsequently silanating the milled glass flakes.

5. The dental composition according to claim 4, wherein the silanating of the milled glass flakes is carried out with a silane having one or more polymerizable groups reactive with the polymerizable compounds (ii).

6. The dental composition according to claim 1, wherein the ratio of the average particle size of the structural filler (A) and the average thickness of the silanated glass flakes (B) is in the range of 10:1 to 1:1.

7. The dental composition according to claim 1, wherein the dental composition contains 1 to 85 percent by weight of the dental filler (i) based on the total weight of the composition.

8. The dental composition according claim 1, wherein the dental composition contains the silanated glass flakes (B) in an amount of from 0.5 to 40 percent by weight based on the total weight of the composition.

9. The dental composition according to claim 1, wherein the ratio of the weight of structural filler (A) and the weight of the silanated glass flakes (B) in the dental composition is in a range of from 80:1 to 0.5:1.

10. The dental composition according to claim 1, wherein the silanated glass flakes (B) have a refractive index in a range of 1.46 to 1.60.

11. The dental composition according to claim 1, wherein the structural filler (A) has a sphericity of at least 0.5.

12. The dental composition according to claim 1, wherein the silanated glass flakes (B) have a particle size distribution determined by light scattering, wherein at least 70 percent of the particles have a particle size of less than 50 μm.

13. The dental composition according to claim 1, wherein:
   the dental composition further comprises a further filler (C) being at least one selected from the group consisting of granulated prepolymerized fillers, ground prepolymerized fillers and filler aggregates; and/or
   the dental composition is a dental composite or a dental cement.

14. A method for preparing a dental composition comprising combining:
   (a) silanated glass flakes having an average thickness between 50 nm and 1000 nm and an average aspect ratio in the range of from 2:1 to 50:1;
   (b) a structural filler having an average particle size of from 0.1 to 3 μm;
   (c) one or more polymerizable compounds; and
   (d) an initiator system.

* * * * *